US010989667B2

(12) United States Patent
Tam

(10) Patent No.: US 10,989,667 B2
(45) Date of Patent: Apr. 27, 2021

(54) UV REFLECTION TESTER

(71) Applicant: Jubilee Diamond Instrument (S) Pte. Ltd., Singapore (SG)

(72) Inventor: Kui Lim Tam, Singapore (SG)

(73) Assignee: Jubilee Diamond Instrument (S) Pte. Ltd., Singapore (SG)

( * ) Notice: Subject to any disclaimer, the term of this patent is extended or adjusted under 35 U.S.C. 154(b) by 0 days.

(21) Appl. No.: 16/496,721

(22) PCT Filed: May 31, 2018

(86) PCT No.: PCT/IB2018/053881
§ 371 (c)(1),
(2) Date: Sep. 23, 2019

(87) PCT Pub. No.: WO2018/220572
PCT Pub. Date: Dec. 6, 2018

(65) Prior Publication Data
US 2020/0249176 A1    Aug. 6, 2020

(30) Foreign Application Priority Data
May 31, 2018  (WO) .................. PCT/IB2018/053881

(51) Int. Cl.
*G01N 21/00* (2006.01)
*G01N 21/87* (2006.01)
*G01N 21/33* (2006.01)
*G01N 21/47* (2006.01)
*G01N 33/38* (2006.01)

(52) U.S. Cl.
CPC ............. *G01N 21/87* (2013.01); *G01N 21/33* (2013.01); *G01N 21/4738* (2013.01); *G01N 33/381* (2013.01); *G01N 2201/02* (2013.01); *G01N 2201/0627* (2013.01)

(58) Field of Classification Search
CPC .... G01N 21/87; G01N 21/33; G01N 21/4738; G01N 33/381; G01N 2201/02; G01N 2201/0627; G01N 21/00
See application file for complete search history.

(56) References Cited

U.S. PATENT DOCUMENTS

| 2,789,430 A | 4/1957 | Sinclaire |
| 4,255,962 A | 3/1981 | Ashman |
| 4,344,315 A | 8/1982 | Moxon et al. |

(Continued)

FOREIGN PATENT DOCUMENTS

| JP | 2015194467 | 11/2015 |
| WO | 8001414 | 7/1980 |

(Continued)

OTHER PUBLICATIONS

Gems & Gemology; Article entitled: "Synthetic Moissanite: A New Diamond Substitute", published Winter 1997, 16 pgs.

(Continued)

*Primary Examiner* — Abdullahi Nur
(74) *Attorney, Agent, or Firm* — Taylor English Duma LLP

(57) ABSTRACT

The application provides a diamond testing device. The testing device includes a casing, a movable specimen holder, an illumination unit, a light sensor unit, and a computing processor. In a closed position, the casing encloses the specimen holder, the illumination unit, and the light sensor unit.

29 Claims, 23 Drawing Sheets

(56) References Cited

U.S. PATENT DOCUMENTS

| | | | |
|---|---|---|---|
| 4,364,677 A | 12/1982 | Ashman | |
| 4,394,580 A | 7/1983 | Gielisse | |
| 4,488,821 A | 12/1984 | Wenckus | |
| 5,164,586 A | 11/1992 | Hohberg et al. | |
| 5,801,819 A | 9/1998 | Spear et al. | |
| 5,835,205 A | 11/1998 | Hunter et al. | |
| 5,883,389 A | 3/1999 | Spear et al. | |
| 5,955,735 A | 9/1999 | Coleman | |
| 6,043,742 A | 3/2000 | Austin | |
| 6,265,884 B1 | 7/2001 | Menashi et al. | |
| 6,439,766 B1 | 8/2002 | Nelson | |
| 7,105,822 B1 | 9/2006 | Beesley | |
| 7,126,351 B2 | 10/2006 | Claus | |
| 7,259,839 B2 | 8/2007 | Sivovolenko | |
| 7,362,109 B2 | 4/2008 | Loginov | |
| 7,382,445 B2 | 6/2008 | Sasian et al. | |
| 8,278,906 B2 | 10/2012 | Loginov et al. | |
| 8,564,316 B2 | 10/2013 | Kessler et al. | |
| 8,749,253 B2 | 6/2014 | Kessler et al. | |
| 8,760,758 B2 | 6/2014 | Verboven et al. | |
| 9,176,068 B1 | 11/2015 | Radomyshelsky et al. | |
| 9,395,350 B2 | 7/2016 | Kessler et al. | |
| 10,161,878 B2 | 12/2018 | Tam | |
| 10,228,330 B2 | 3/2019 | Tam | |
| 10,247,677 B2 | 4/2019 | Tam | |
| 10,859,559 B1 | 12/2020 | Tam | |
| 2001/0023925 A1 | 9/2001 | Smith | |
| 2004/0008888 A1 | 1/2004 | Patton et al. | |
| 2005/0213203 A1* | 9/2005 | Harrison | G02B 21/242 359/383 |
| 2006/0044823 A1 | 3/2006 | Wong et al. | |
| 2006/0087306 A1 | 4/2006 | Loginov | |
| 2006/0098187 A1 | 5/2006 | Claus | |
| 2012/0007619 A1 | 1/2012 | Zhu et al. | |
| 2012/0049836 A1 | 3/2012 | Kessler et al. | |
| 2012/0059619 A1 | 3/2012 | Zhu et al. | |
| 2012/0274751 A1 | 11/2012 | Smith et al. | |
| 2014/0337035 A1 | 11/2014 | Kessler et al. | |
| 2015/0015877 A1 | 1/2015 | Smith et al. | |
| 2015/0091593 A1 | 4/2015 | Zhu et al. | |
| 2015/0219567 A1 | 8/2015 | Sim et al. | |
| 2016/0178168 A1 | 6/2016 | Didur | |
| 2016/0178530 A1 | 6/2016 | Davies et al. | |
| 2016/0290930 A1 | 10/2016 | Takahashi | |
| 2016/0363576 A1 | 12/2016 | Zhu et al. | |
| 2018/0238811 A1 | 8/2018 | Tam | |
| 2019/0011373 A1 | 1/2019 | Tam | |
| 2019/0072495 A1 | 3/2019 | Tam | |
| 2020/0400646 A1 | 12/2020 | Tam | |

FOREIGN PATENT DOCUMENTS

| | | |
|---|---|---|
| WO | 2014055041 | 4/2014 |
| WO | 2015007873 | 1/2015 |
| WO | 2017025825 | 2/2017 |
| WO | 2017208053 | 12/2017 |
| WO | 2018150221 | 8/2018 |
| WO | 2019122955 | 6/2019 |

OTHER PUBLICATIONS

Gems & Gemology; Symposium proceedings issue entitled: "Proceedings of the Third International Gemological Symposium", published Fall 1999, 185 pgs.
Tam, Kui Lim; International Preliminary Report for Patentability for PCT/IB2016/054071, filed Jul. 7, 2016, dated Nov. 28, 2017, 4 pgs.
Tam, Kui Lim; International Search Report and Written Opinion for PCT/IB2016/054071, filed Jul. 7, 2016, dated Oct. 26, 2016, 11 pgs.
Tam, Kui Lim; Issue Notification for U.S. Appl. No. 15/751,529, filed 219/2018, dated Dec. 5, 2018, 1 pg.
Tam, Kui Lim; Notice of Allowance for U.S. Appl. No. 15/751,529, filed Feb. 9, 2018, dated Oct. 3, 2018, 13 pgs.
Tam, Kui Lim; Notice of Allowance for U.S. Appl. No. 15/751,529, filed Feb. 9, 2018, dated Aug. 23, 2018, 14 pgs.
Tam, Kui Lim; Supplemental Notice of Allowance for U.S. Appl. No. 15/751,529, filed Feb. 9, 2018, dated Sep. 11, 2018, 12 pgs.
Tam, Kui Lim; Issue Notification for U.S. Appl. No. 16/176,059, filed Oct. 31, 2018, dated Mar. 13, 2019, 1 pg.
Tam, Kui Lim; Non-Final Office Action for U.S. Appl. No. 16/176,059, filed Oct. 31, 2018, dated Dec. 27, 2018, 15 pgs.
Tam, Kui Lim; Notice of Allowance for U.S. Appl. No. 16/176,059, filed Oct. 31, 2018, dated Feb. 6, 2019, 12 pgs.
Tam, Kui Lim; International Preliminary Report on Patentability for PCT/IB2016/053208, filed Jun. 1, 2016, dated Oct. 11, 2018, 7 pgs.
Tam, Kui Lim; International Search Report for PCT/IB2016/053208, filed Jun. 1, 2016, dated Feb. 28, 2017, 3 pgs.
Tam, Kui Lim; Issue Notification for U.S. Appl. No. 16/128,610, filed Sep. 12, 2018, dated Feb. 20, 2019, 1 pg.
Tam, Kui Lim; Non-Final Office Action for U.S. Appl. No. 16/128,610, filed Sep. 12, 2018, dated Nov. 13, 2018, 19 pgs.
Tam, Kui Lim; Notice of Allowance for U.S. Appl. No. 16/128,610, filed Sep. 12, 2018, dated Jan. 4, 2019, 7 pgs.
Tam, Kui Lim; International Search Report Report and Written Opinion for PCT/IB2017/050803, filed Feb. 14, 2017, dated Oct. 25, 2017, 14 pgs.
Tam, Kui Lim; International Search Report and Written Opinion for PCT/IB2017/058093, filed Dec. 19, 2017, dated Sep. 19, 2018, 12 pgs.
Zeiss; Article entitled: "Education in Microscopy and Digital Imaging", published as early as Dec. 23, 2008, located at <https://web.archive.org/web/20081223034455/http://zeiss-campus.magnet.fsu.edu/articles/lightsources/tungstenhalogen.html>, 9 pgs.
Tam, Kui Lim; International Preliminary Report on Patentability for PCT/IB2018/053881, filed May 31, 2018, dated Aug. 7, 2019, 4 pgs.
Tam, Kui Lim; International Search Report and Written Opinion for PCT/IB2018/053881, filed May 31, 2018, dated Oct. 29, 2018, 20 pgs.
Tam, Kui Lim; Notice of Allowance for U.S. Appl. No. 16/988,914, filed Aug. 10, 2020, dated Sep. 17, 2020, 20 pgs.
Jubilee Diamond Instrument(S) Pte Ltd; Office Action for India patent application No. 201947037061, filed Sep. 14, 2019, dated Feb. 25, 2021, 5 pgs.

* cited by examiner

UV REFLECTION TESTER

The present specification relates to an ultraviolet (UV) reflection tester which is capable of detecting possible synthetic diamonds by means of evaluating UV light reflected back within a specimen.

In order to know whether a diamond specimen is a natural or a synthetic diamond, gemologists can use a detector device to shine a predetermined amount of ultraviolet (UV) light onto the diamond specimen. The diamond specimen then absorbs or reflects the UV light. The detector device then measures amount of the reflected UV light. If the specimen reflects a predetermined amount of the UV light from the specimen, the specimen is inferred to be a type IIa, or IaB natural diamond, or a potentially synthetic diamond. If the specimen does not reflect the predetermined value of UV light from the specimen, the specimen is inferred to be a type IaA, or IaAB natural diamond.

It is an object of the application to provide an improved diamond tester. The diamond tester is also called a diamond testing device.

The diamond tester can be used for assessing both loose cut diamonds, such as melee diamonds, and jewelries such as ring, necklace, and ear rings.

The diamond tester works by evaluating light being reflected back from a diamond specimen. In one aspect of the application, the diamond tester measures amount of UV light reflected from the diamond specimen.

The application provides an improved diamond testing device.

The testing device includes a casing with an opening, a specimen holder with a resilient means, a cover with an ultraviolet (UV) lamp, a light sensor unit, and a gemstone evaluation board. The lamp refers to a light source. The gemstone is also called gem stone.

In detail, the opening defines a gemstone testing area. The specimen holder is movable attached to the casing and it is provided in the testing area. The cover is pivotably attached to the casing. The light sensor unit is fixedly attached to the casing and it is also provided in the testing area. The light sensor unit comprises an UV light sensor.

In use, the specimen holder is intended for receiving a gemstone specimen, such as diamond specimen. The gemstone specimen can be provided on a finger ring, a necklace, or an ear ring. It can also be provided in a loose form.

The UV lamp generates UV light rays, which are directed at the gemstone specimen.

The cover is rotated such that it shields a user from the UV light rays. These light rays can harm eyes of the user. The cover also prevents the specimen from receiving ambient light rays, wherein the ambient light rays can affect testing of the gemstone.

The resilient means serves to bias or push the specimen holder towards the light sensor unit. The pushing serves to place the light sensor near to the specimen.

The light sensor acts to receive the UV light rays, which are reflected from within the gemstone specimen. The light sensor then generates signal according to received light rays.

The evaluation board then evaluates the specimen according to signals from the light sensor unit. In detail, the evaluation board determines type of gemstone.

This arrangement provides a testing device, which is simple, low cost and easy to produce.

The application provides another improved diamond testing device.

The diamond testing device includes a casing with an opening, a specimen holder with a resilient means, an illumination bar with an ultraviolet (UV) lamp, a detachable cover, a light sensor unit, the light sensor unit comprises an UV light sensor, and an evaluation board.

In detail, the opening defines a testing area. The specimen holder is movable attached to the casing and is provided in the testing area. The illumination bar is pivotably attached to the casing. The light sensor unit is attached to the casing and is provided in the testing area In use, the specimen holder receives a gemstone specimen.

The UV lamp illuminates the specimen. In other words, the UV lamp generates UV light rays, which are directed at the specimen.

The detachable cover shields a user from the UV light rays of the UV lamp.

The resilient means biases or pushes the specimen holder towards the light sensor unit.

The light sensor unit receives the UV light rays, which are reflected from the specimen. The light sensor unit then generates signals according the received UV light rays.

The evaluation board evaluates the specimen according to signals from the light sensor unit. In detail, the evaluation board determines type of gemstone.

This arrangement provides another testing device, which is simple, low cost and easy to produce.

The light sensor unit can include one or more long wavelength light sensors while the diamond testing device includes a long wavelength illumination unit. This arrangement provides another means of testing the specimen with light rays of long wavelength.

Different ways of arranging the long wavelength light sensor and the ultraviolet light sensor are possible.

According one aspect of the application, the long wavelength light sensor and the ultraviolet light sensor are provided on a revolver table with a revolver mechanism. The revolver mechanism acts to rotate the revolver table for selectively placing the long wavelength light sensor and the ultraviolet light sensor at different predetermined rotational positions for receiving corresponding light rays, which are reflected from the specimen in order to determine a characteristic of the specimen.

Different implementations of the long wavelength light sensor and the long wavelength illumination unit are possible.

In one implementation, the long wavelength light sensor comprises a visible light sensor while the long wavelength illumination unit comprises a visible light emitter.

The visible light emitter can be provided as a visible light LED (Light Emitting Diode), which can be obtained easily.

In another implementation, the long wavelength light sensor comprises an infrared light sensor while the long wavelength illumination unit comprises an infrared light emitter.

The infrared light emitter can be provided as an IR LED.

The long wavelength illumination unit can include a ring-shaped holder with alternating visible light emitters and infrared light emitters for saving space.

The ring-shaped holder can surround the light sensor unit for easy design.

The long wavelength light sensor and the UV light sensor can be moved to a detection/testing position that is provided above the sensor tube by means of an electric motor or a revolver table.

An electronic circuit is often adapted to move the specimen holder into a long wavelength testing position, which is provided at a predetermined distance away from a tip of the light sensor unit.

The light sensor unit can include a sensor tube for easy design.

The light sensor unit can include a testing tube which protrudes towards the specimen holder.

The resilient means often includes a helical metal spring.

An accumulator, such as capacitor or a rechargeable battery, can be provided for energizing the UV lamp. The accumulator is connected to an electrical high-power circuit for providing energy to the accumulator.

The UV lamp can be provided as a tube lamp, such as gas discharge lamp, although other means are also possible.

In general, the UV lamp can be provided an UV light emitter, such as a UV LED.

The UV lamp can generate light rays with a wavelength, which ranges from about 240 nm (nanometre) to about 268 nm.

The visible light emitter can generate light rays with a wavelength, which ranges from about 380 nm to about 780 nm.

The infrared light emitter can generate light rays with a wavelength, which ranges from about 750 nm to about 1,000,000 nm.

In detail, the light rays can include near-infrared light rays with a wavelength that ranges from about 750 nm to about 1,400 nm, short-wavelength infrared light rays with a wavelength that ranges from about 1,400 nm to about 3,000 nm, mid-wavelength infrared light rays with a wavelength that ranges from about 3,000 nm to about 8,000 nm, long-wavelength infrared light rays with a wavelength that ranges from about 8,000 nm to about 15,000 nm, and far-infrared light rays with a wavelength that ranges from about 15,000 nm to about 1,000,000 nm.

The infrared or long-wavelength light rays can be used to determine whether a specimen is a diamond or other type of stones.

If the specimen reflects the infrared light rays with an intensity that is above a predetermined value, the specimen is then inferred to be a diamond. If the specimen reflects the infrared wave with an intensity that is below the predetermined value, the specimen is then inferred to be other types of stones.

After this, the specimen, which is inferred to be a diamond, can be subjected to further test using a UV lamp for determining whether the diamond specimen is an earth mined diamond or an HPHT/CVD diamond.

The application provides an improved diamond testing device. The diamond testing device includes a casing, a movable specimen holder, an illumination unit, a light sensor unit, and a computing processor.

Referring to the casing, it includes a stationary base unit with a cover unit that is pivotably attached to the base unit.

The casing can be placed in an open position and in a closed position. In the closed position, the cover unit is moved such that the casing fully enclosed a specimen testing area.

Referring to the movable specimen holder, it includes a vertically movable specimen receiving unit and a resilient element. The vertically movable specimen receiving unit is provided in the specimen testing area for receiving a diamond specimen. The specimen receiving unit is movably attached to the base unit.

The specimen refers to a diamond. The diamond can be a natural diamond that is produced using geological process or be an artificial diamond that is produced using a man-made process.

The resilient element is provided inside the stationary base unit for urging and pushing vertically the specimen receiving unit and the diamond specimen to a predetermined specimen testing position.

Referring to the illumination unit, it includes an ultraviolet (UV) light emitting diode (LED) light source. The light source is also called a lamp. The UV LED light source is attached to the base unit and it is placed above the predetermined specimen testing position. The UV LED light source is used for generating UV light rays with a predetermined light intensity, in which the UV light rays is directed at the diamond specimen that is provided at the predetermined specimen testing position.

Referring to the light sensor unit, it includes an elongated vertical detector tube and a light detector.

The elongated vertical detector tube is attached to the base unit and it is placed near the UV LED light source and placed in the specimen testing area. It is also placed vertically above the predetermined specimen testing position for receiving the UV light rays being reflected from the diamond specimen. The detector tube acts to guide or direct the received UV light rays from one end of the detector tube to another end of the detector tube.

The light detector is used for measuring intensity of the UV light rays, which travel through the detector tube.

Referring to the computing processor, it is provided for activating the LED light source to generate UV light rays with a predetermined light intensity. After this, it receives measurements of the UV light rays from the light detector. These UV light rays are reflected from the diamond specimen. The processor then generates a result signal according to the measurements and sends out the result signal.

This diamond testing device provides several benefits.

The UV LED light source generates UV light rays in a brief time. This is different from other light sources that uses other technology, which require a long warm up time. This, in turn, allows for a quick evaluation of the diamond specimen.

The UV LED light source is positioned near the diamond specimen and near the detector tube, thereby allowing for more efficient illumination of the diamond specimen.

The UV LED light source and the detector tube are also stationary and are fixed to the casing base unit. This improves reliability of the diamond testing device. This is different from other testing devices, wherein its light source is attached a moving part of the testing device. In use, the movement of the part can cause the part to fail earlier.

The diamond testing device can be adapted easily to receive large pieces of jewelry.

This diamond testing device provides diamond evaluation result quickly. The user can be trained quickly to use the diamond testing device. A long training is not needed to differentiate a natural diamond from a synthetic diamond.

The diamond testing device can include several features, which are described below.

The movable specimen holder often includes a movable specimen positioning button. The specimen positioning button is placed next to an outer surface of the base unit. The specimen positioning button is connected to the resilient element or the vertically movable specimen receiving unit. A user can actuate or move the specimen positioning button for moving the resilient element and the vertically movable specimen receiving unit vertically away from the predetermined specimen testing position. This then allows the user to place a diamond specimen easily on the specimen receiving unit.

The resilient element can include a spring unit, although it can also include other resilient means.

The specimen receiving unit can include a rotatable holder ring with at least one specimen receiving area. The specimen receiving area is intended for receiving a diamond specimen.

The specimen receiving area are placed on an outer surface of the rotatable holder ring. The shape of the specimen receiving area corresponds to the shape of the diamond specimen, such that the diamond specimen can rest securely on the specimen receiving area.

The specimen receiving area can comprise a recess with an opening. The recess is used for receiving an elongated straight stud of an earring such that a diamond specimen of the earring rest securely on the opening. In effect, the stud does not block the earring, thereby allowing the earring to be placed properly and securely for evaluation. This is different from other diamond testers.

The specimen receiving unit can also include a stationary inner cylinder. The inner cylinder is attached to the base unit and it is inserted inside the holder ring for engaging and for supporting the holder ring. This arrangement then allows the holder ring to rotate the specimen receiving area to a desired position. This is especially useful, when the holder ring has more than one specimen receiving area.

The light sensor unit often includes a sensor housing for enclosing the light detector and for blocking external light rays from reaching the light detector. Put differently, the housing enables the light detector to receive only light rays from the detector tube and to receive only light rays reflected from the diamond specimen and not from other sources.

The detector tube is adapted such that it is positioned for contacting the diamond specimen, which is provided in the specimen receiving area of the specimen receiving unit, wherein the specimen receiving unit that is placed in the predetermined specimen testing position.

The diamond testing device often includes a plurality of indicator light sources. The indicator light sources are provided on the casing. The indicator light sources are intended to be selectively activated according to the result signal. This allows a user to know the diamond specimen result by viewing or looking at the activated indicator light sources.

The diamond testing device can also include a test activation button being providing on the casing. A user can press the test activation button to send a test activation signal to the computing processor.

In one aspect of the application, the diamond testing device includes a cover position switch for providing an indication of a position of the casing to the computing processor. In detail, the cover position switch provides two states, namely a closed state and an open state. When the casing is open, the casing places the cover position switch in one state. When the casing is closed, the casing places the cover position switch in another state. The computing processor can then detect the position of the casing from data regarding the state of the cover position switch.

In one implementation, the base unit comprises a horizontal base part and a vertical base part. One end of the horizontal base part is attached to a lower end of vertical base part such that the base unit has a L shape. Similarly, the cover unit comprises a lower cover part and an upper cover part. An upper end of the lower cover part is attached to a first end of the upper cover part such that the cover unit has an L shape. A second end of the upper cover part is pivotable attached to an upper end of the vertical base part.

In one implementation, the cover unit is rotatably connected to the base unit via a vertical pin.

The subject of the present specification is now explained in more detail with respect to the following Figs:

Figure 6:
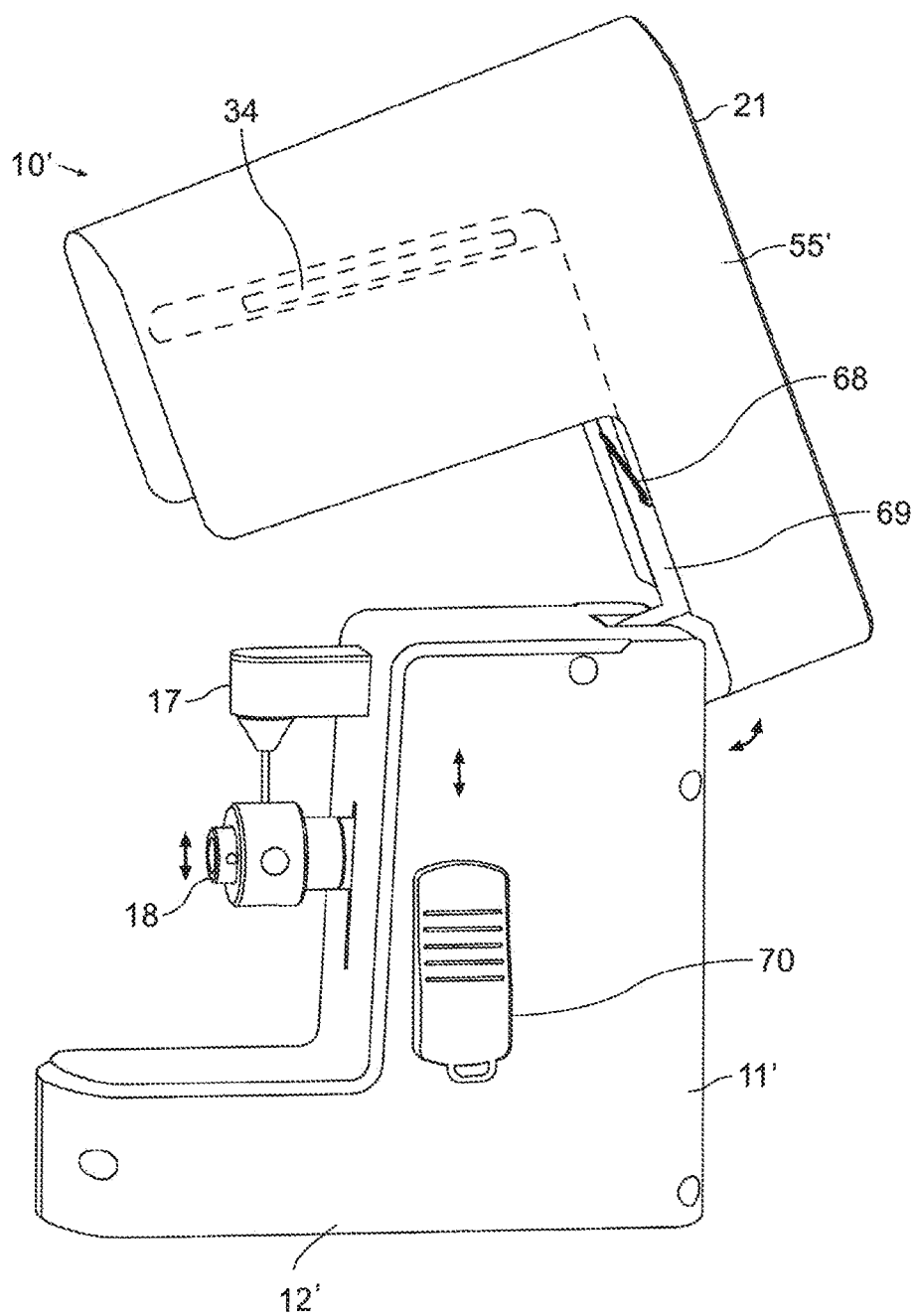
Figure 7:
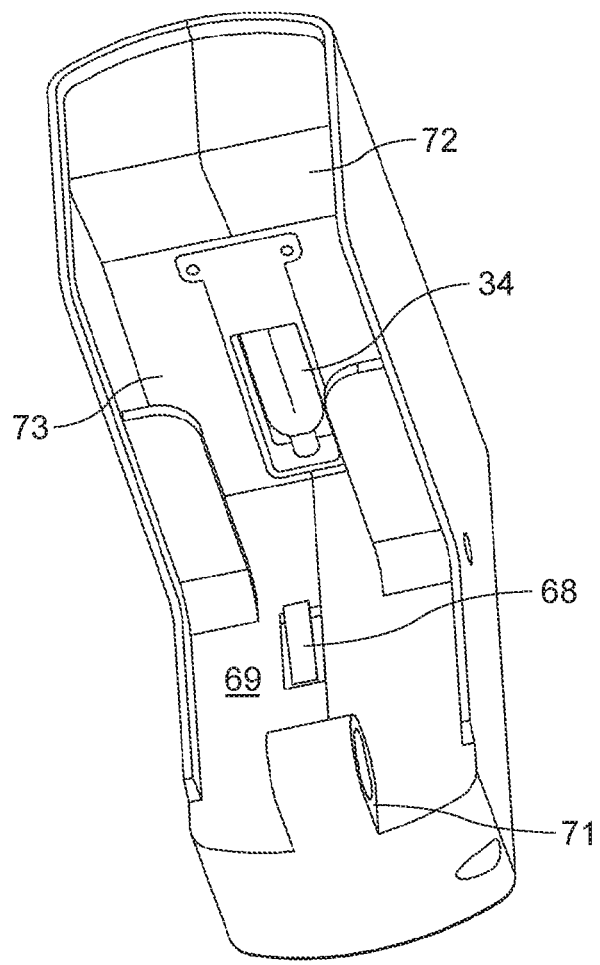
Figure 8:
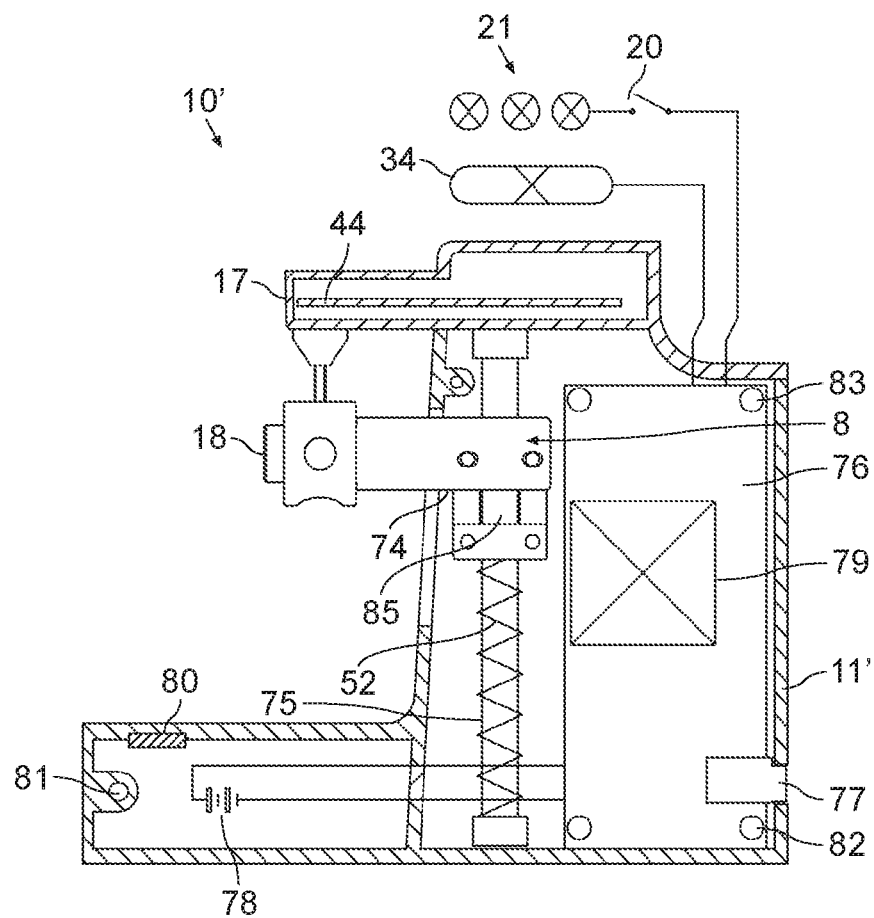
Figure 9:
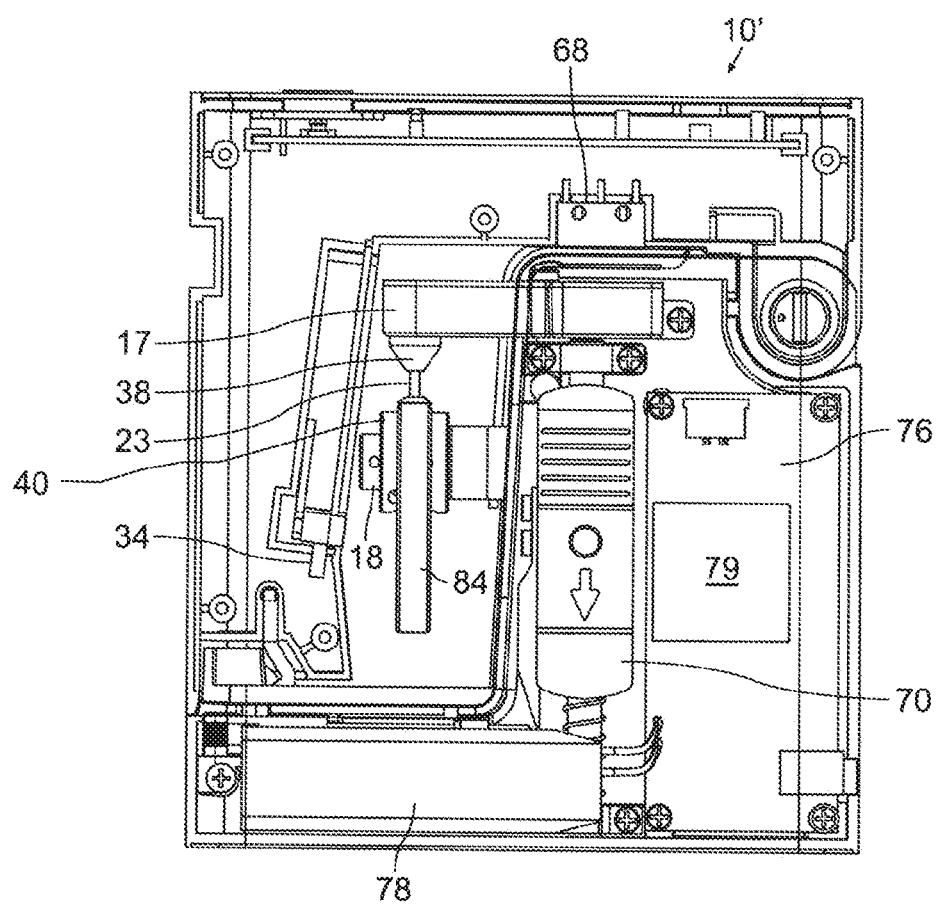
Figure 10:
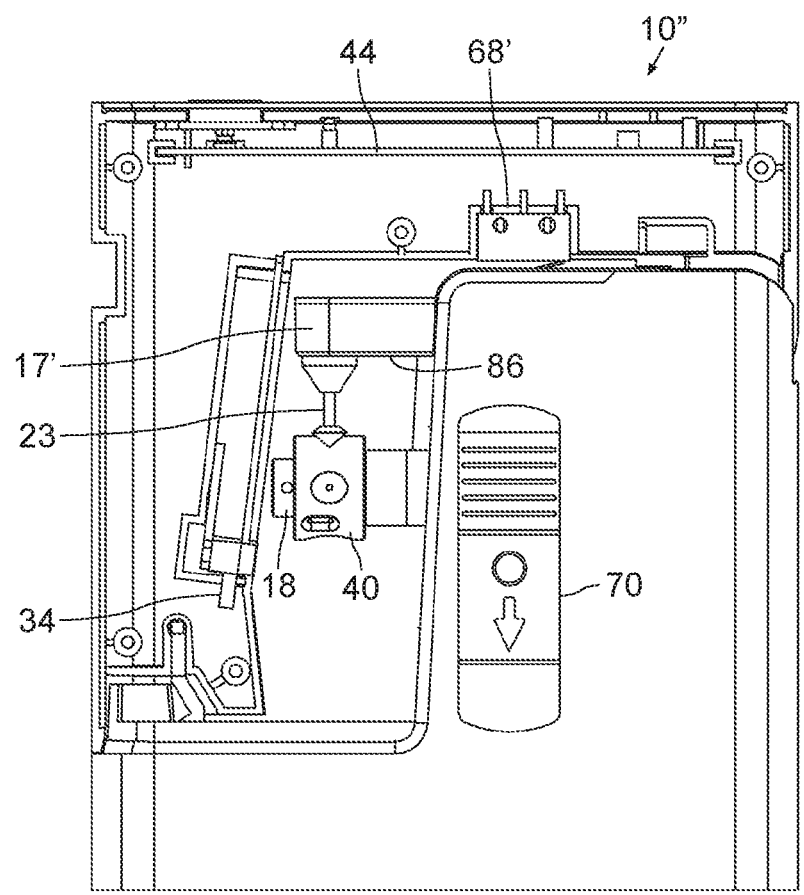
Figure 11:
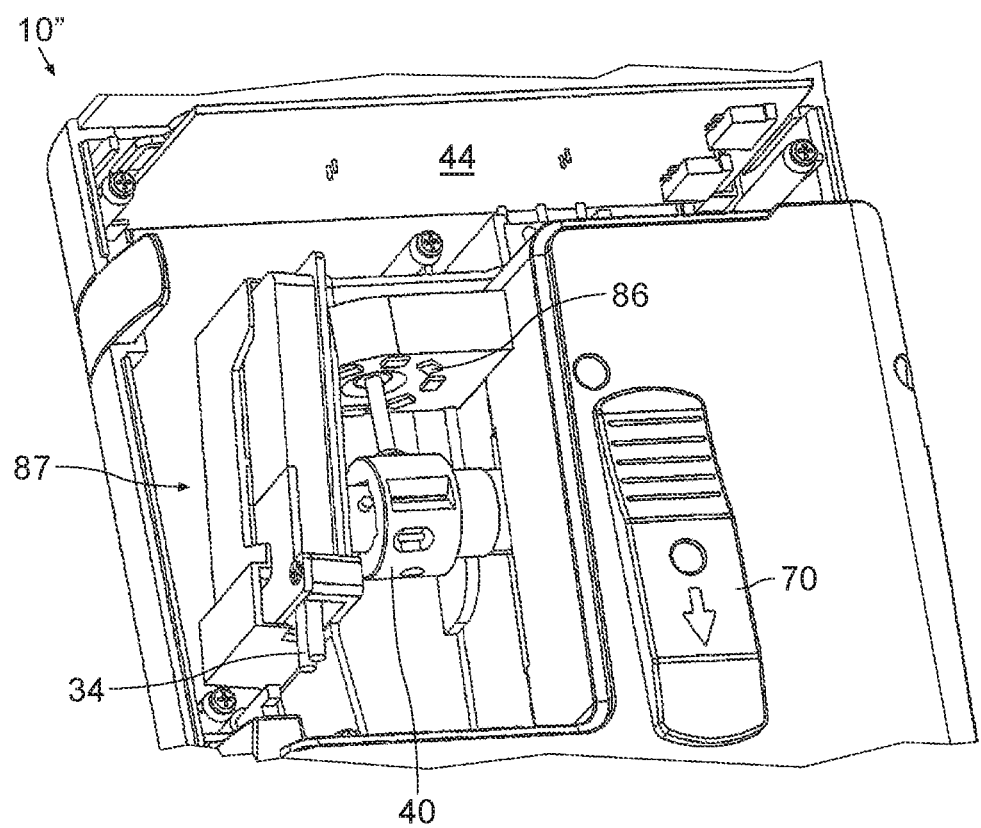
Figure 12:
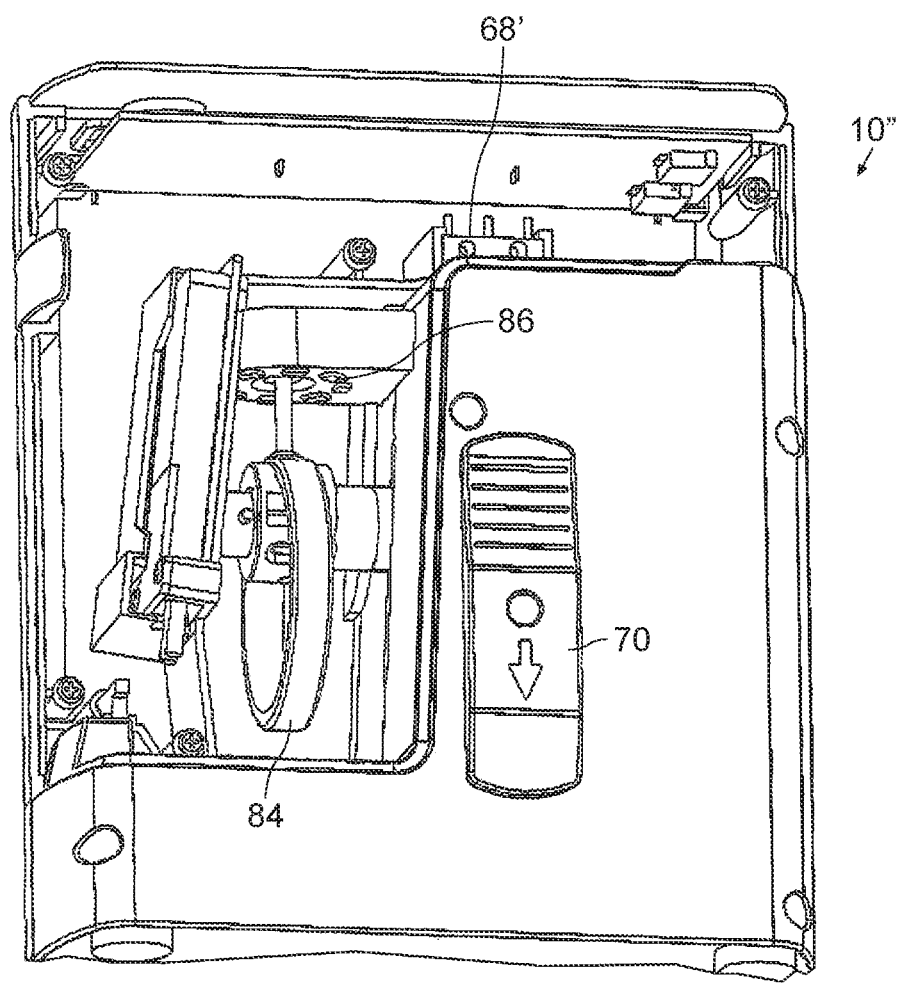
Figure 13:
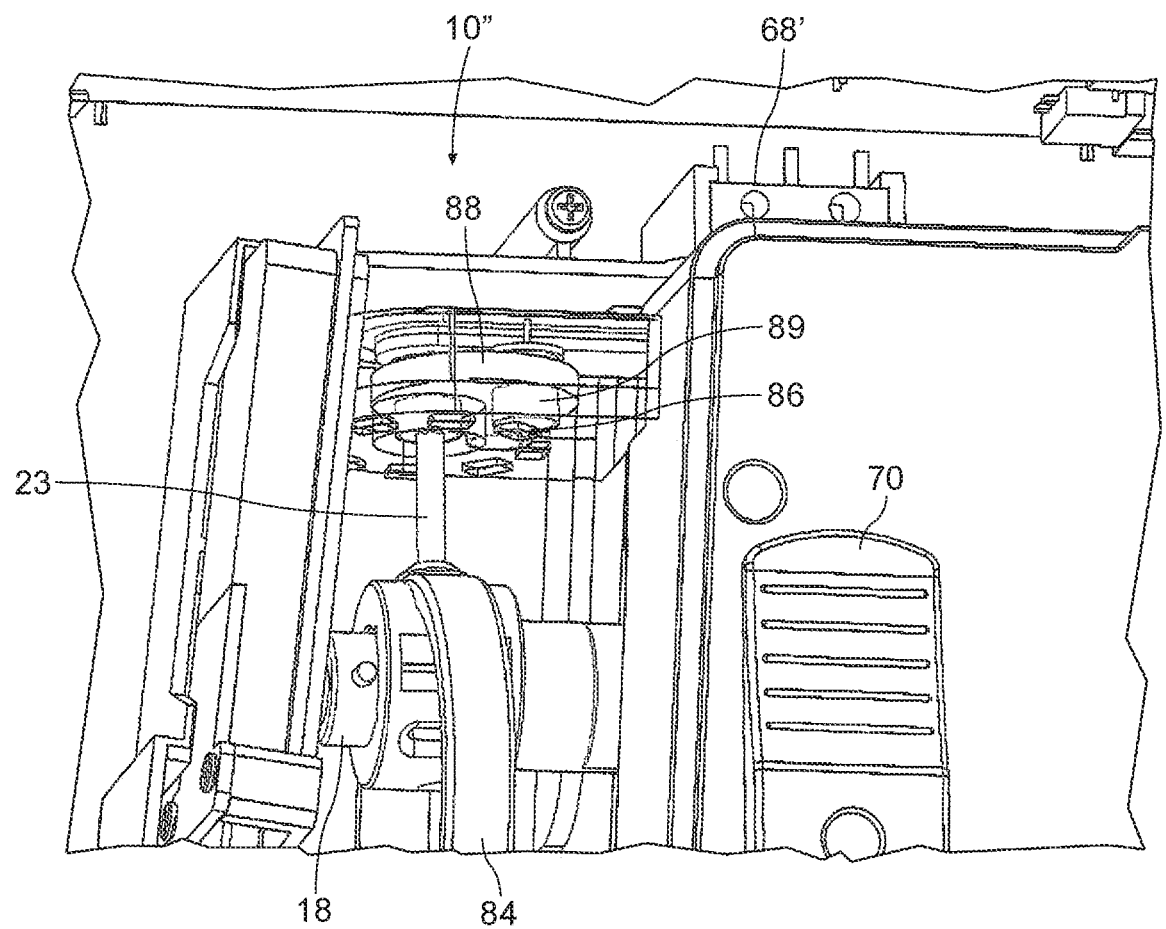
Figure 14:
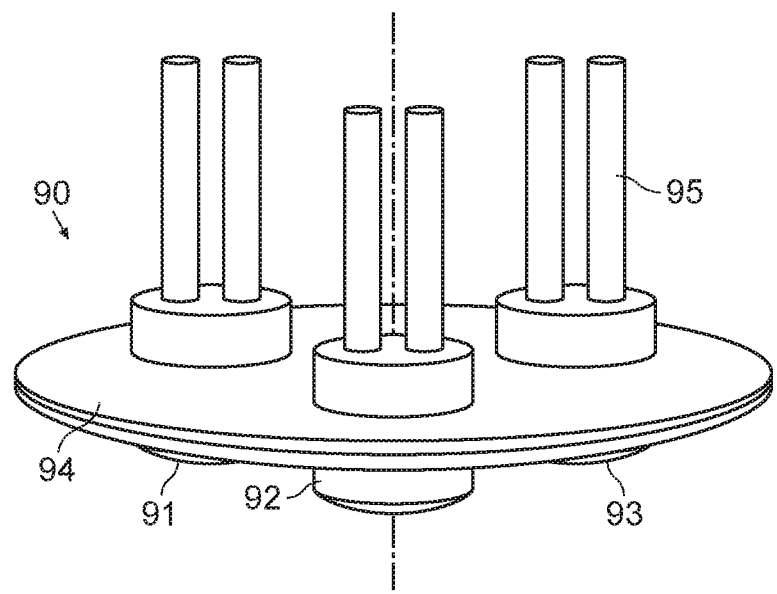
Figure 15:
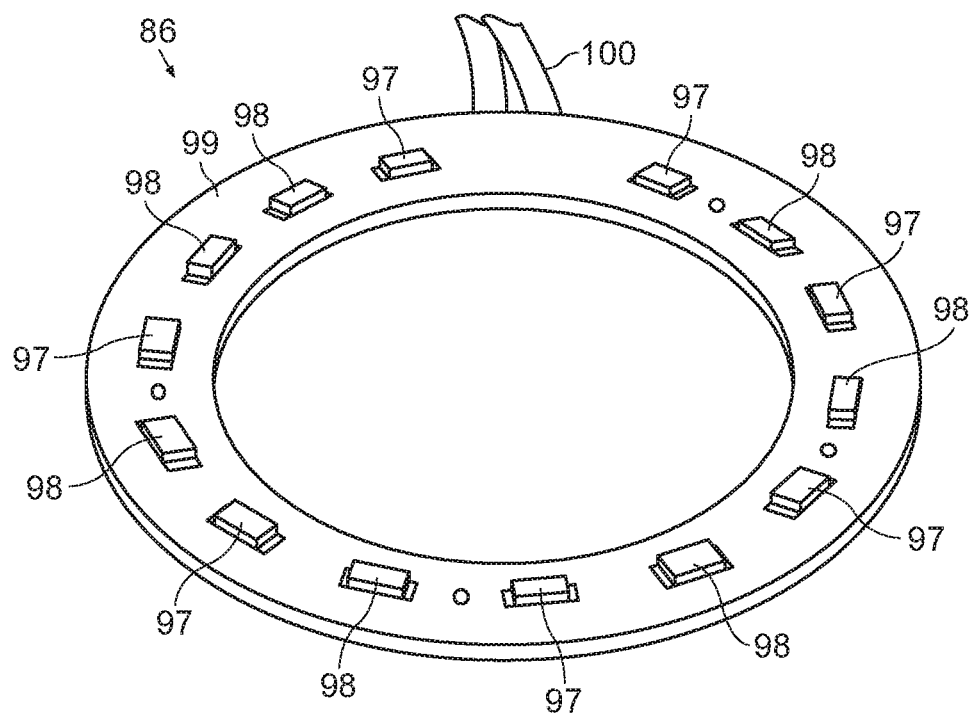
Figure 16:
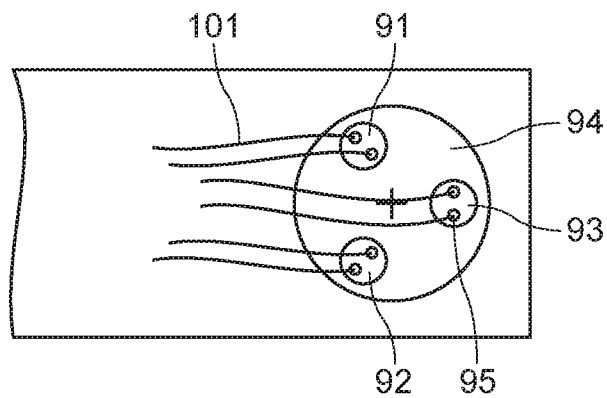
Figure 17:
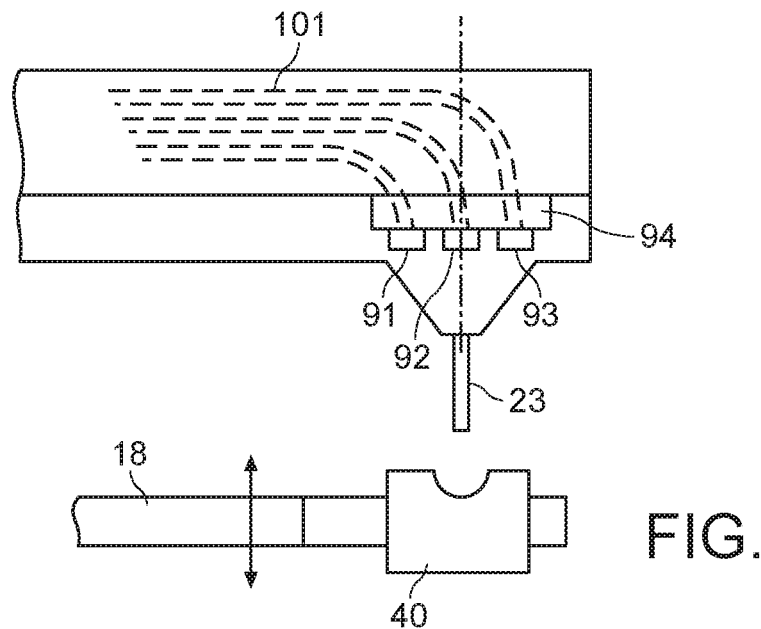
Figure 18:
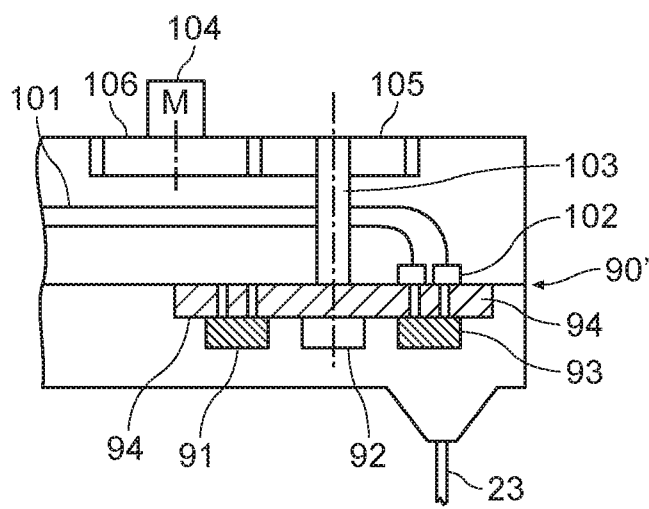
Figure 19:
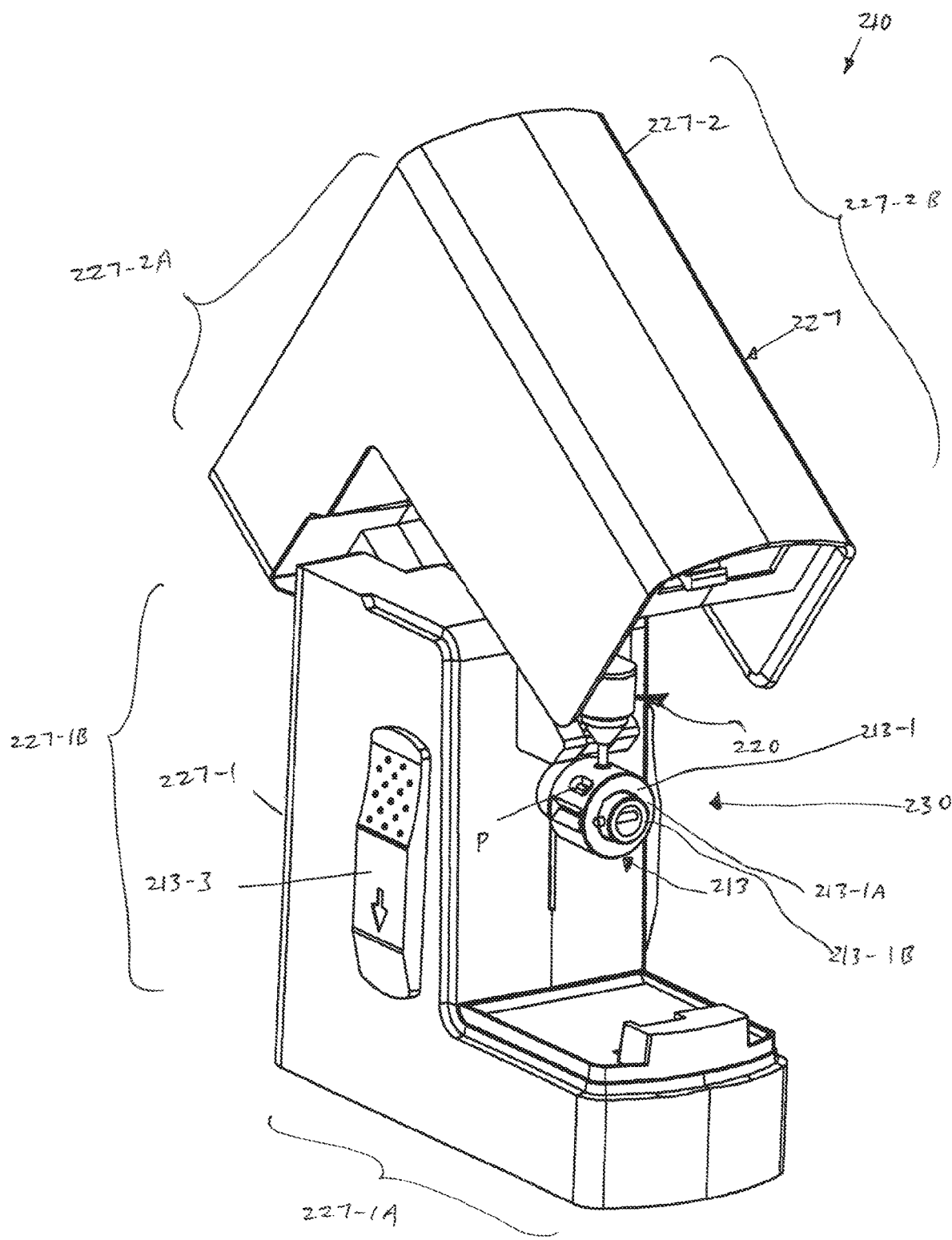
Figure 20:
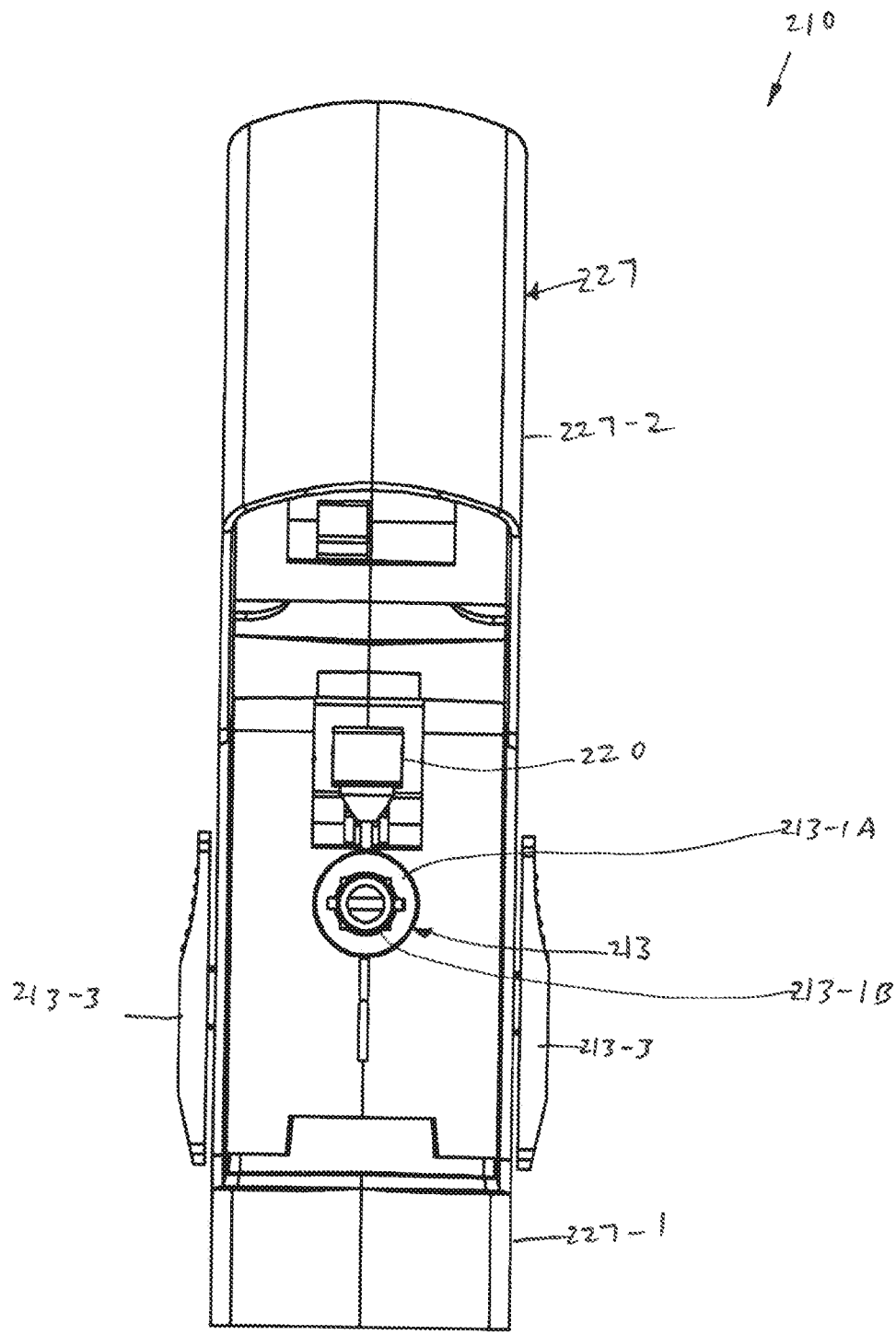
Figure 21:
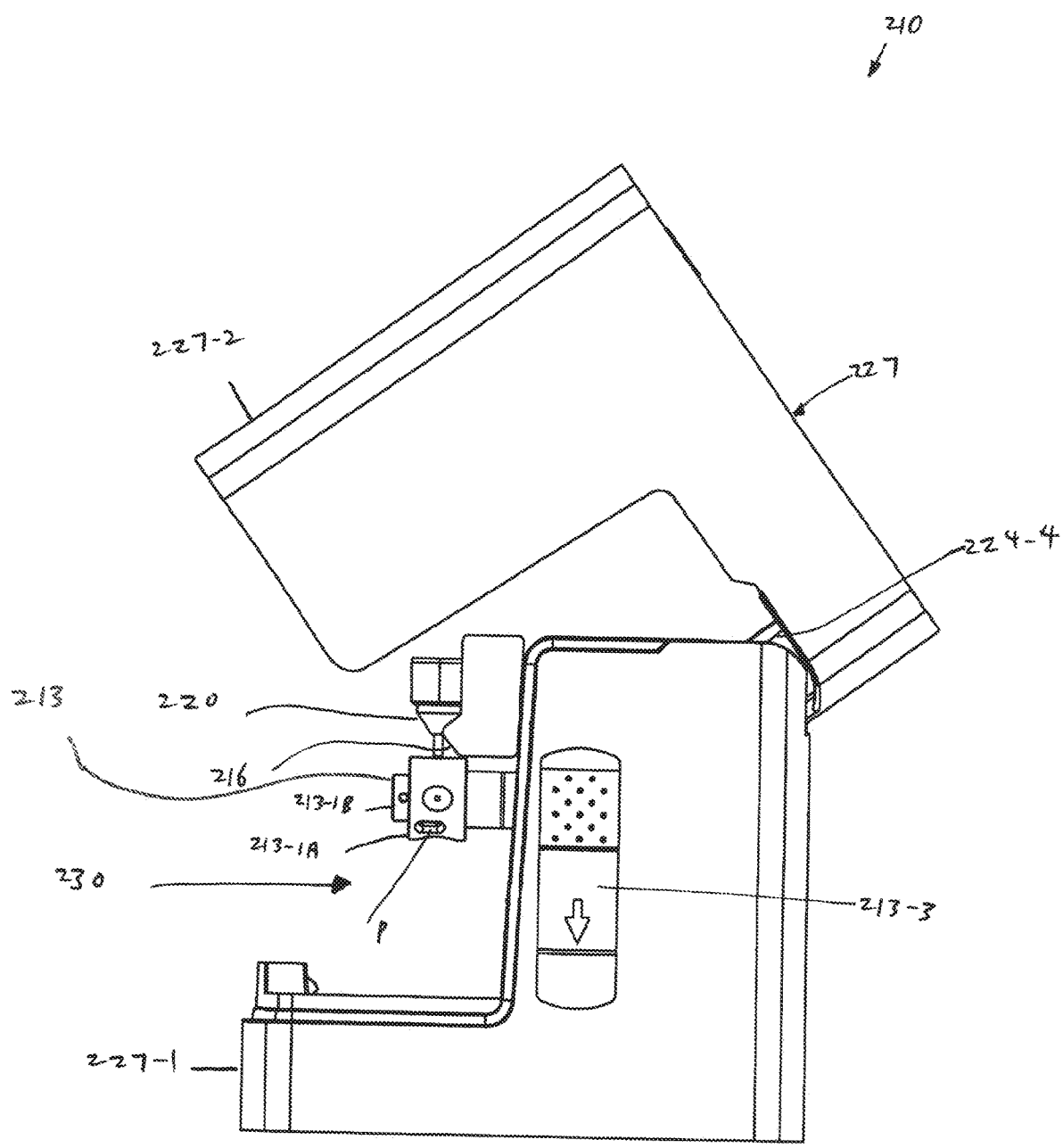
Figure 22:
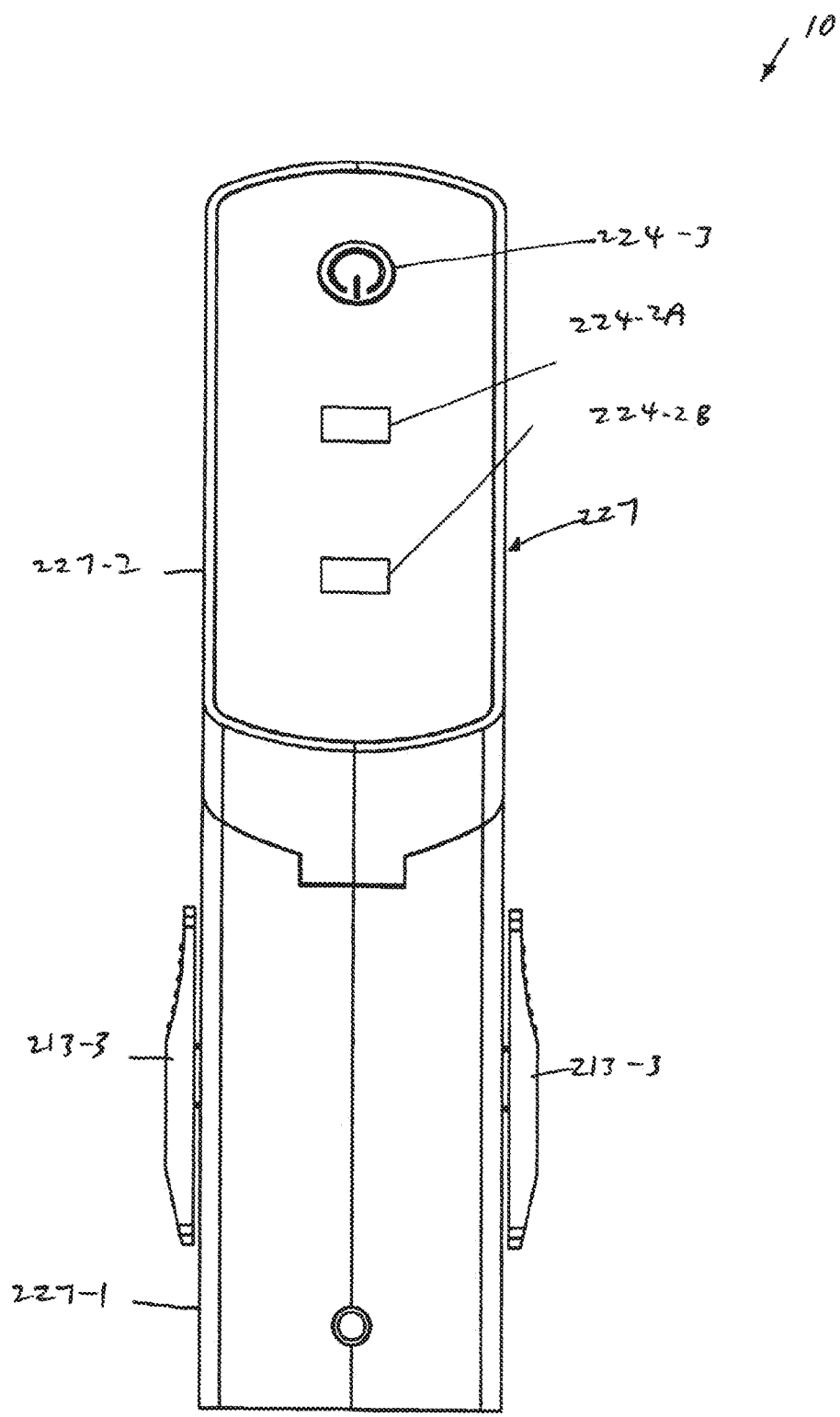
Figure 23:
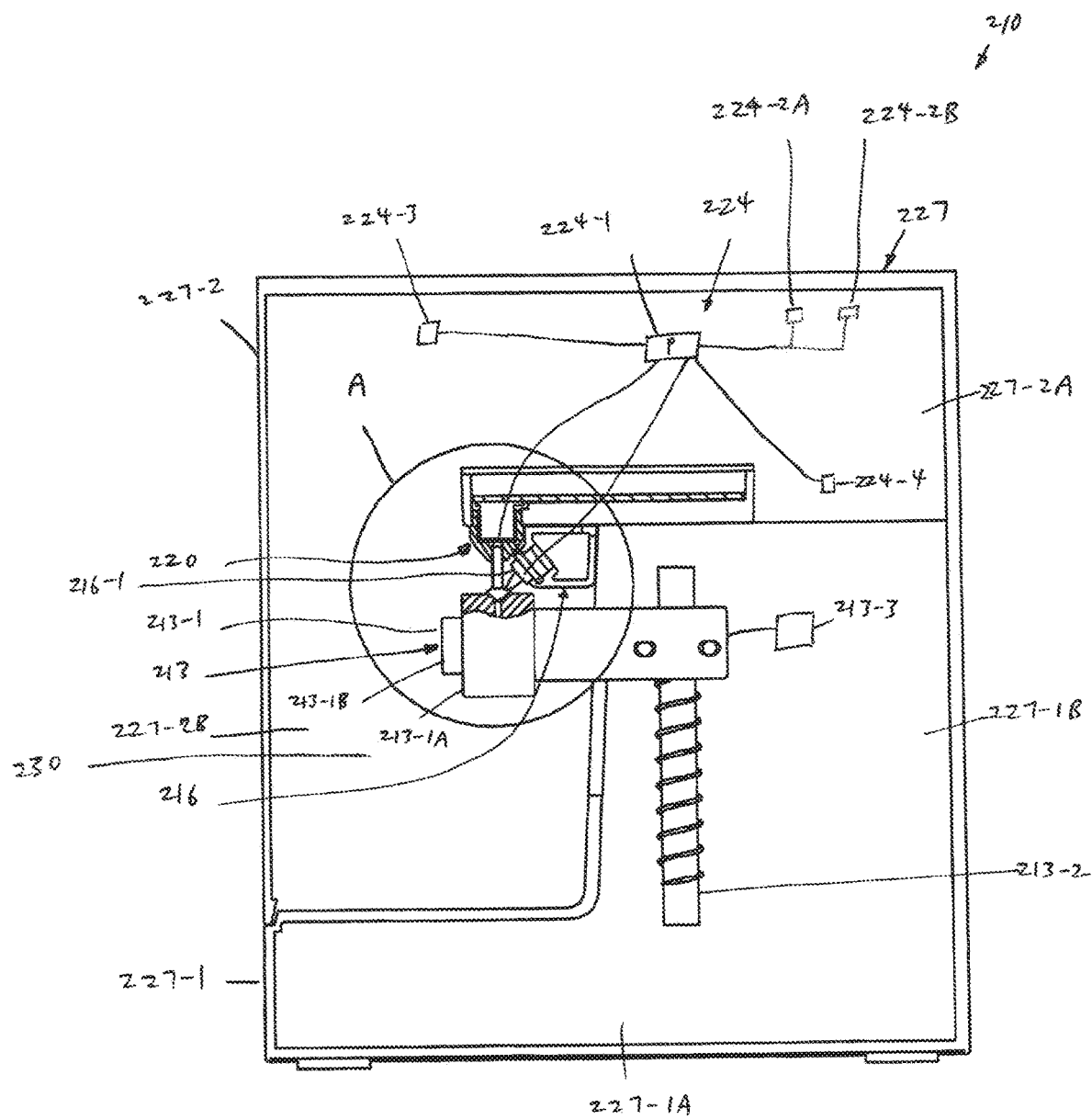
Figure 24:
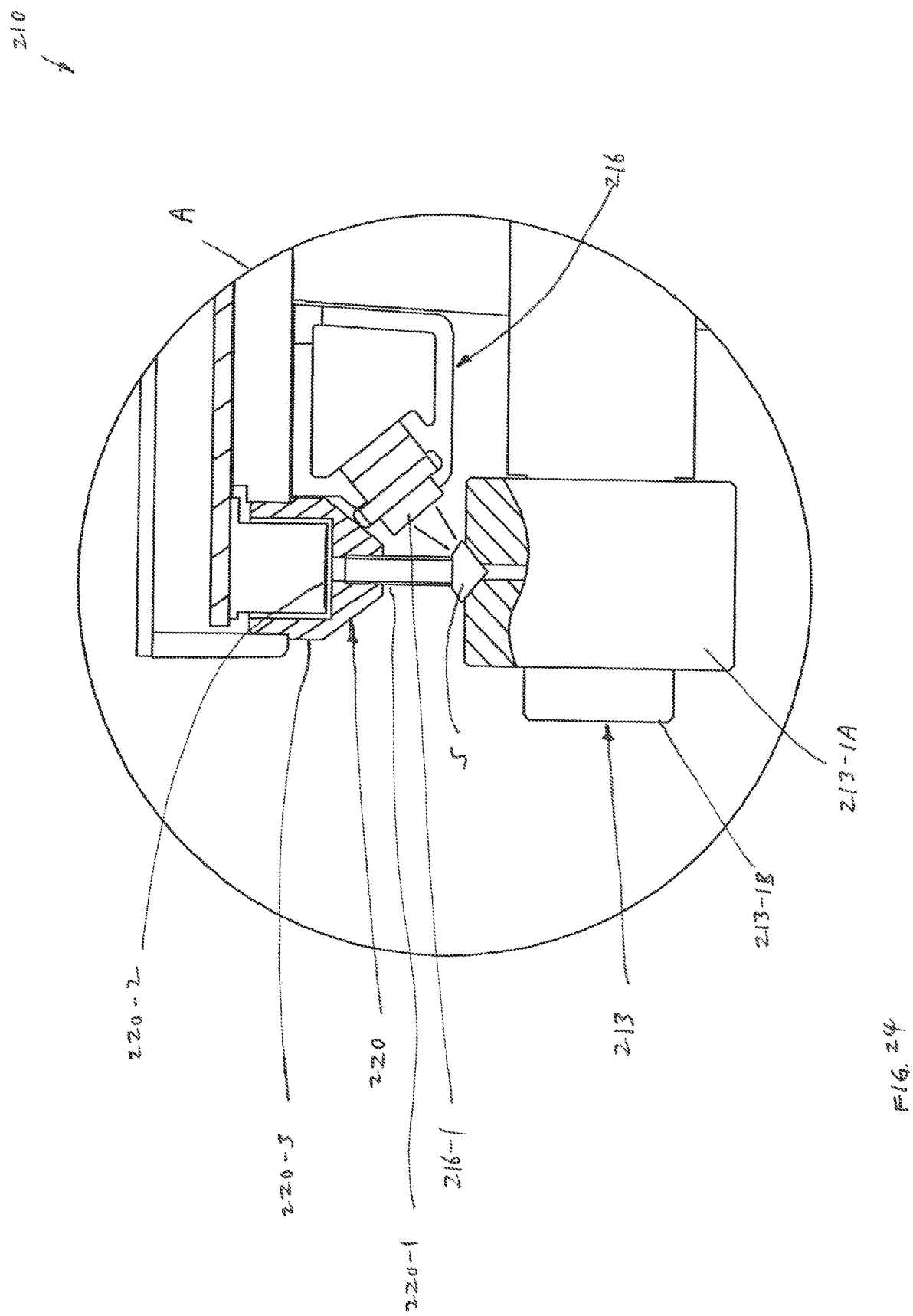
Figure 25:
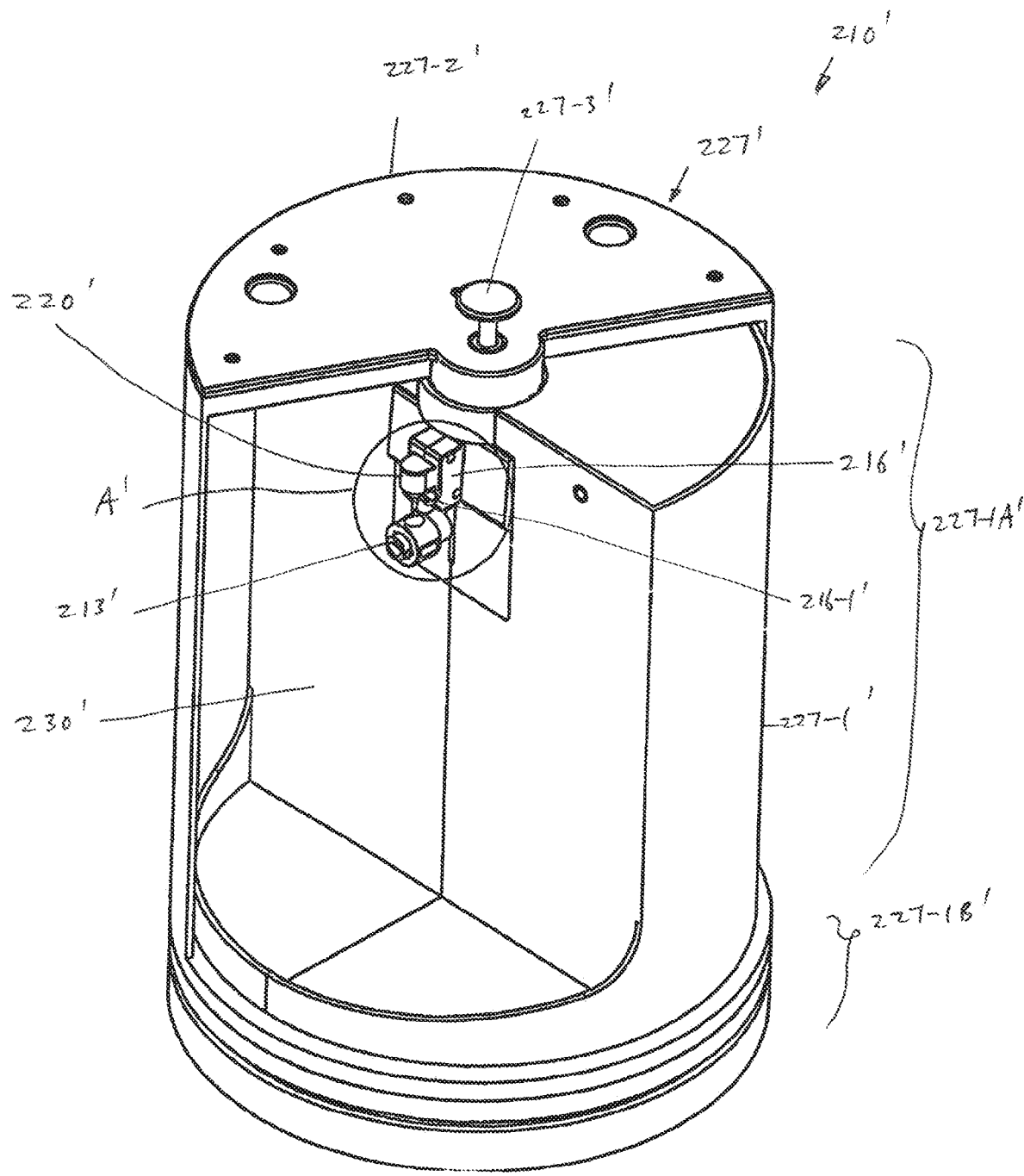
Figure 26:
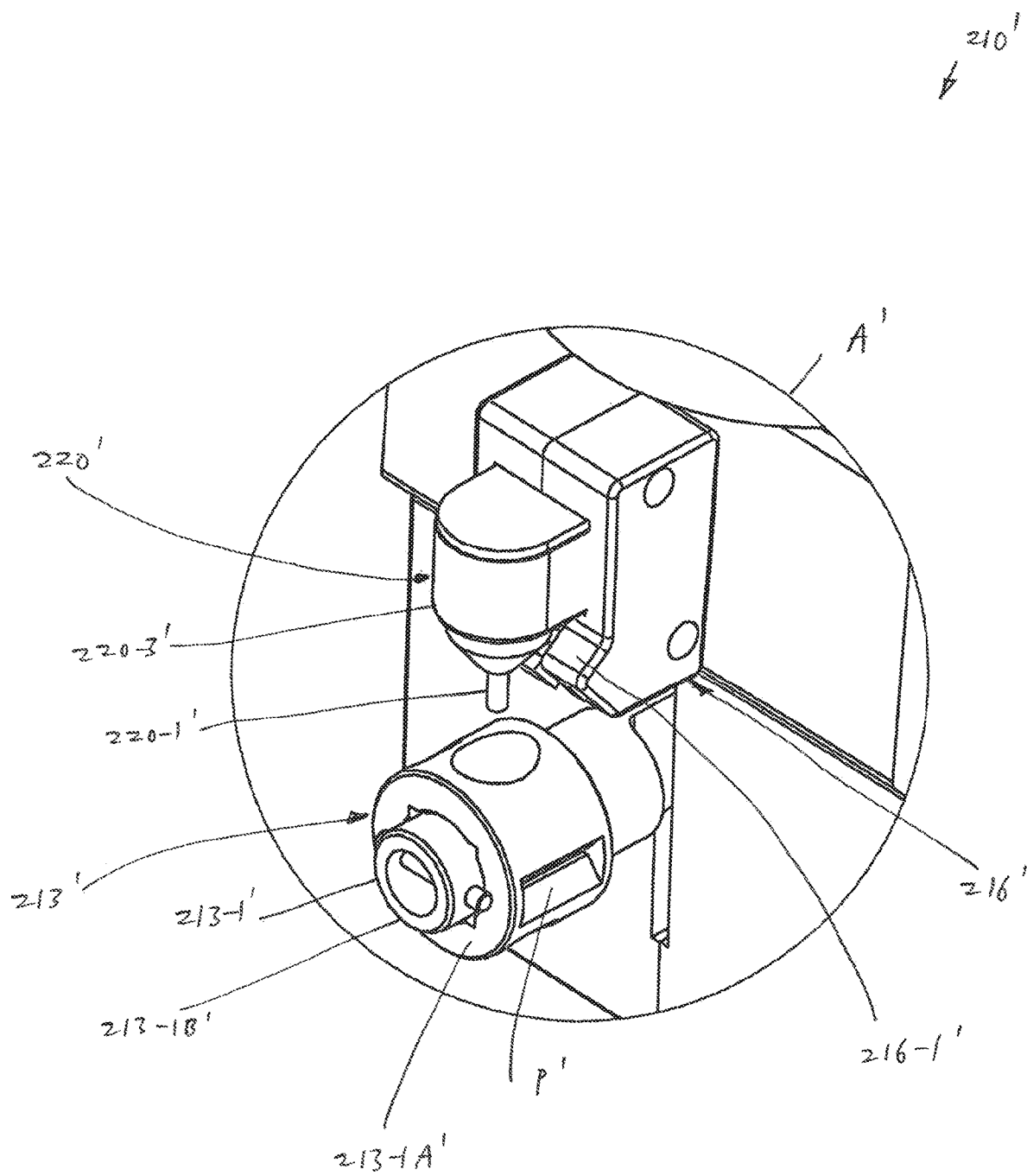
Figure 27:
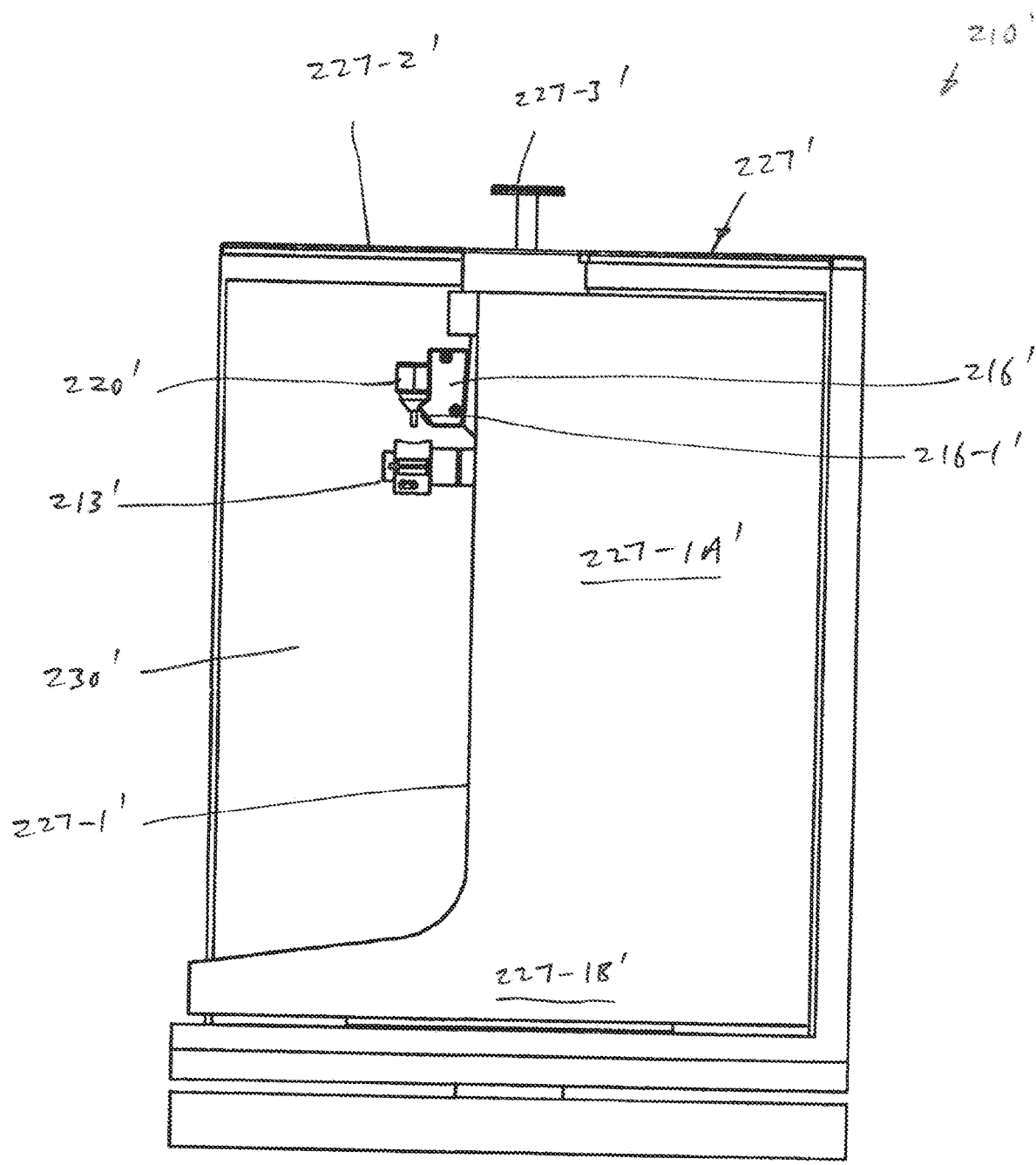

FIG. 6 shows a further embodiment of the UV reflection tester with a pivotable cover, FIG. 7 shows a view of the pivotable cover of the UV reflection tester of FIG. 6, and FIG. 8 shows a cross sectional view of the UV reflection tester of FIG. 6, FIG. 9 shows a further view of the UV reflection tester of FIG. 6, FIG. 10 shows a further embodiment of a UV reflection tester, which is similar to the UV reflection tester of FIGS. 6 to 9, FIG. 11 shows a sectional perspective view of the UV reflection tester of FIG. 10, FIG. 12 shows a further sectional perspective view of the UV reflection tester of FIG. 10, FIG. 13 shows an enlarged sectional view of FIG. 12, FIG. 14 shows a revolver mechanism for a light detector for use in the reflection tester of FIGS. 10 to 13, FIG. 15 shows a ring-shaped arrangement of visible light and IR detector for use in the reflection tester of FIGS. 10 to 13, FIG. 16 shows a top view of the revolver mechanism of FIG. 14, FIG. 17 shows a side view of the revolver mechanism of FIG. 14 and a portion of the reflection tester, FIG. 18 shows a further embodiment of the revolver mechanism and a portion of the reflection tester, FIG. 19 illustrates a perspective view of a diamond tester, FIG. 20 illustrates a front view of the diamond tester of FIG. 19, FIG. 21 illustrates a side view of the diamond tester of FIG. 19, FIG. 22 illustrates a rear view of the diamond tester of FIG. 19, FIG. 23 illustrates a side cross-sectional view of the diamond tester of FIG. 19, FIG. 24 illustrates an expanded view of a part of the diamond tester of FIG. 23, FIG. 25 illustrates a perspective view of a further diamond tester, which is a variation of the diamond tester of FIG. 19, FIG. 26 illustrates an expanded view of a part of the diamond tester of FIG. 25, and FIG. 27 illustrates a side view of the diamond tester of FIG. 25.

In the following description, details are provided to describe the embodiments of the specification. It shall be apparent to one skilled in the art, however, that the embodiments may be practised without such details.

Some embodiments have similar parts. The similar parts may have the same names or similar part reference numerals with an alphabet or prime symbol. The description of one part also applies by reference to a similar part, where appropriate, thereby reducing repetition of text without limiting the disclosure.

FIGS. 1 to 5 show a first embodiment of a UV reflection tester 10.

An illumination bar 16, a sensor unit 17 and a specimen holder 18 are arranged within the testing area 15. The illumination bar 16 is pivotably supported by a pivot joint in the top portion 14 of the plastic casing 11. The pivot joint, which is not shown in FIG. 1, is provided above the sensor unit 17 In FIG. 1, a pivotal movement of the illumination bar 16 is indicated by a double arrow 26.

Figure 1:
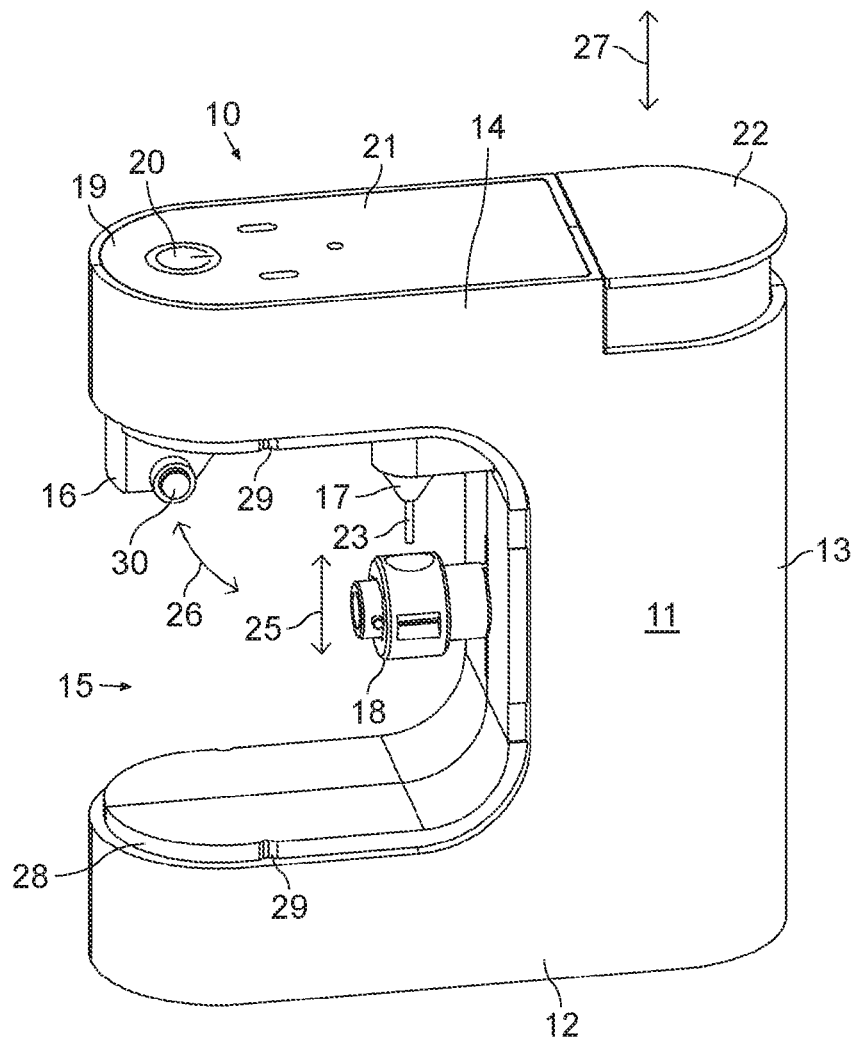
FIG. 1 shows a side view of a UV reflection tester without a cover.

FIG. 1 shows a side view of the UV reflection tester 10 in which a detachable cover is removed. The UV reflection tester 10 comprises a plastic casing 11 which has a bottom portion 12, a side portion 13 and a top portion 14. A U-shaped recess 15 is formed out between the bottom portion 12 and the top portion 14. The U-shaped recess 15 provides a testing area 15 for a specimen.

The sensor unit 17 is provided at the top of the testing area 15 and at an inner side of the plastic casing 11, which is next to the side portion 13. The specimen holder 18 is provided below the sensor unit 17 and protrudes into the testing area 15 from the side portion 13 of the plastic casing 11. Furthermore, the specimen holder 18 is horizontally supported in the side portion 13 of the plastic casing 11 such that is vertically movable upwards and downwards. In FIG. 1 the movement of the specimen holder 18 is indicated by a double arrow 25.

A top surface 19 of the top portion 14 of the casing comprises an on/off switch 20, an indicator or indicator area 21 and a heel-shaped push button 22. The push button 22 is vertically movable upwards and downwards. Furthermore, the push button 22 is connected to the specimen holder 18 such that the specimen holder 18 moves together with the push button 22 in the vertical direction. The push button 22 is biased towards an upward position by a spring or other resilient means, which is not shown in FIG. 1, wherein the specimen holder 18 is biased against a tip 23 or detector tube 23 of the sensor unit 17. In FIG. 1, the movement of the push button 22 is indicated by a double arrow 27.

Here and in the following embodiments, a minimum distance is provided between the specimen holder 18 and the detector tube 23.

Here and in the following embodiments, the specimen holder 18 can be made of a reflective material.

Figure 2:
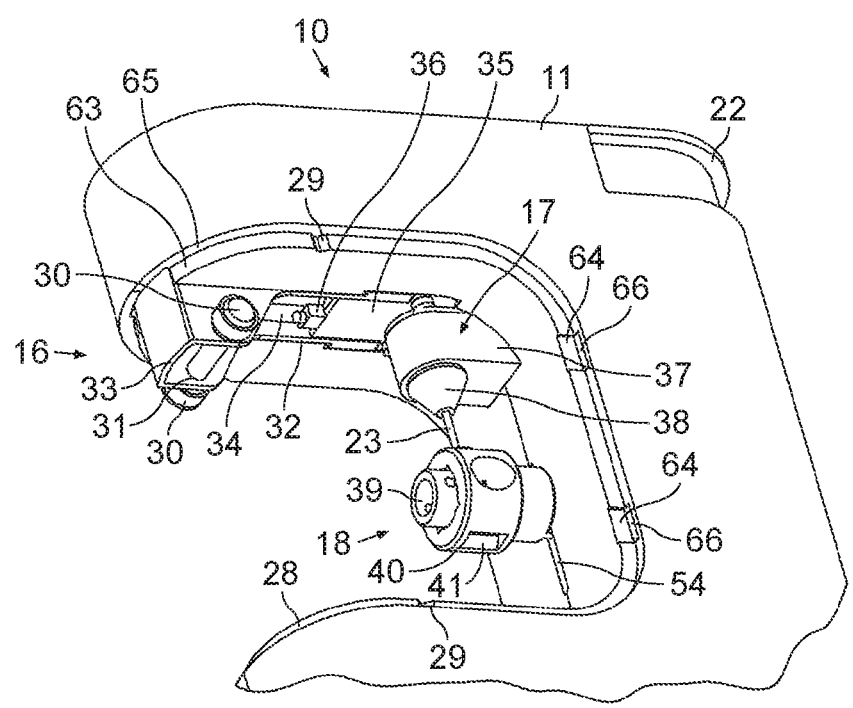
FIG. 2 shows a bottom-up view of the UV reflection tester of FIG. 1.
Figure 4:
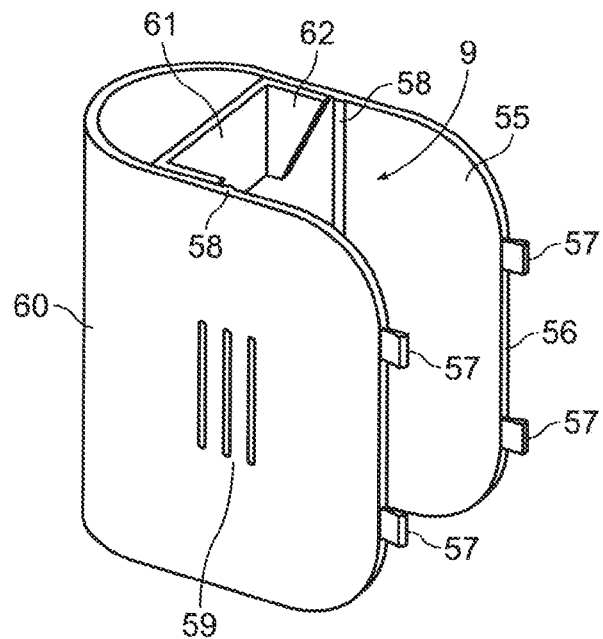
FIG. 4 shows a detachable cover of the UV reflection tester of FIG. 1.

The U-shaped testing area 15 is bounded by an engagement ledge 28. An inner side 63 of the engagement ledge 28 comprises round engagement recesses 29 at opposite sides of a horizontal portion of the inner side 63. The inner sided 63 is shown in FIG. 2. Elongated recesses 64 are provided at a vertical portion of the inner side 63. An outer side 65 of the engagement ledge 28 comprises engagement slots 66. The engagement ledge 28 is provided for engagement with a detachable cover 55, which is shown in FIG. 4.

In FIG. 2, the illumination bar 16 is shown in a rest position in which it is taken up by an opening of the plastic casing 11. The illumination bar 16 has the shape of a U-profile which comprises a base portion 32 and a head portion 33. The head portion 33 of the illumination bar 16 comprises at an actuation bar 31 which has actuation disks 30 that are placed at outer ends of the actuation bar 31.

Figure 3:
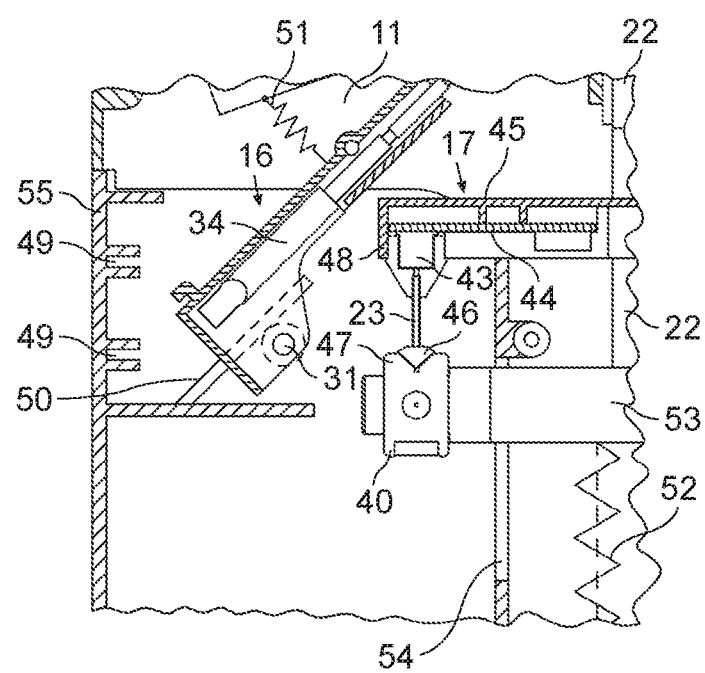
FIG. 3 shows a sectional partial view of the UV reflection tester of FIG. 1.

In the rest position, the head portion 33 protrudes downwards from the plastic casing 11. The illumination bar 16 is biased towards its rest position by a spring or other resilient means which is shown in FIG. 3.

In an engaged position, the detachable cover 55 is moved onto the testing area 15 and towards the engagement ledge 28. A ramp on the detachable cover 55 then pushes against the actuation disk 30 and moves the illumination bar 16 downwards into its operating position. In this engaged position, the detachable cover 55 shields the surroundings of the UV reflection tester 10 from ultraviolet radiation. A security switch is later actuated when the detachable cover 55 is in the engaged position. The security switch enables the device to run a test on a specimen.

Furthermore, the illumination bar 16 comprises a tube lamp 34 which is connected to a power electronic circuit 35 via an intermediate component 36. The intermediate component 36 is an LED for energizing the tube lamp 34. The tube lamp 34 is capable of emitting ultraviolet light.

The sensor unit 17 comprises an upper portion 37, which protrudes from the plastic casing 11 into the testing area 15, a cone shaped portion 38, which protrudes downwards from the upper portion 37, and the detector tube 23.

The specimen holder 18 comprises a conductive inner cylinder 39 which protrudes horizontally from the plastic casing 11 and a conductive holder ring 40 which is arranged around the inner cylinder 39. The holder ring 40 comprises four cone shaped pockets 41, which are suitable for taking up a specimen or an inwardly protruding portion of a ring. The holder ring 40 can be turned around its axis, such that a respective pocket 41 can be arranged below the detector tube 23. The pockets 41 are formed as conical shapes of three different sizes and as a rectangular wedge, respectively.

Preferentially, the holder ring 40 has a diameter that is smaller than a finger ring, such that the ring can be placed conveniently around the holder ring 40. The specimen holder 18 extends through a vertical slit 54 which is provided in the side portion 13 of the plastic casing 11. The vertical slit 54 is horizontally centred in an inner side of the plastic casing 11.

FIG. 3 shows a sectional view of the UV reflection tester 10. An inner structure of the sensor unit 17 and the illumination bar 16 is shown. The upper portion of the sensor unit 17 comprises an upper part 45, a front part 48, a circuit board 44 and a UV detector 43, which is arranged between a circuit board 44 and the detector tube 23. The UV detector 43 is electrically connected to the circuit board 44. Furthermore, FIG. 3 shows a gemstone 46 to be tested, which is placed on a testing platform 47 that is formed out on the holder ring 40. The gemstone 46 is also called a gem stone.

On the left-hand side of FIG. 3 the detachable cover 55 is shown in its inserted position. The detachable cover 55 comprises attachment portions 49 for attaching a ramp 50.

Furthermore, FIG. 3 shows a first biasing spring 51, which is attached to the plastic casing 11 and to the illumination bar 16, and a second biasing spring 52, which is attached to the plastic casing 11 and to a holding bar 53 of the specimen holder 18. The specimen holder 18 moves under the force of a spring into a testing position. If the specimen has at least a minimum predetermined height it abuts to both the specimen holder 18 and the detector tube 23 in the testing position.

The pivotable cover 55 is closed and the UV lamp 34 is activated. The UV detector 43 receives the portion of the UV radiation that passes through the specimen. Based on the received light intensity, an evaluation circuit, which may be provided on the circuit board 44, determines the type of the specimen and indicates the result in the indicator area 21.

According to one evaluation method, a diamond is detected as an earth mined diamond if the received intensity is below a predetermined threshold and is detected as a possibly synthetic diamond, such as an HPHT diamond or a CVD diamond, if the received intensity is above the predetermined threshold. A preceding decision regarding the diamond may be based on the reflection spectrum, for example on characteristic minima of reflection.

Preferentially, the specimen holder 18 is a movable part which is biased upwardly against the stationary detector tube 23. However, in alternative embodiments, the detector tube 23 may be provided as a movable part which is biased downwards against a stationary specimen holder 18.

When a specimen is to be tested, the specimen holder 18 is lowered using the push button 22 and the specimen is placed onto the holder ring 40. Afterwards, the push button 22 is released again and the specimen is pressed against the tip 23 of the sensor unit 17. The detachable cover 55 is moved towards the engagement ledge 28, whereby the illumination bar 16 is moved downwards into its operation position and the security switch is actuated. Next, the UV tube lamp 34 is activated using the on/off switch 20. Reflected light from within the specimen is sensed by the UV detector 43. A measurement circuit of the sensor unit 17 evaluates the measured light intensity and the result is displayed in the indicator area 21 at the top surface 19 of the plastic casing 11.

Specifically, the UV lamp 34 can be designed to emit light mainly in the wavelength range from 240 nm to 268 nm, especially in a range about 254 nm, for example in the range of 254+/−10 nm or in the range of 254+/−5 nm. Herein the range can be defined, for example, by a light frequency range which contains 90% of luminous flux or a light frequency range in which light intensity is more than 5% of the peak light intensity. The UV lamp 34 can be provided by a tube lamp, as shown in the embodiment, or it can be provided by another type of UV lamp. Specifically, the UV lamp can be provided by a UV LED.

FIG. 4 shows a detachable cover 55 for use in the UV reflection tester 10 of FIG. 1. The detachable cover 55 has a U-shaped profile. The shape of a rim 56 of the detachable cover 55 matches with the shape of the engagement ledge 28 of the plastic casing 11. Furthermore, the rim 56 of the detachable cover 55 comprises rectangular protrusions 57 which fit into the engagement slots 66 of the plastic casing 11. Two ridges 58 with half circular cross sections are arranged at an inner side 9 of the detachable cover 55. The two ridges 58 match with the respective round recesses of the engagement ledge 28.

An outer surface 60 of the detachable cover 55 comprises vertically aligned handling ripples 59. At the bottom of the U-shaped profile, an actuation element 61 which has ramp shaped portions 62. The ramp shaped portions 62 correspond to the ramp 50 that is shown schematically in FIG. 3.

Due to the size and the U-shaped profile of the detachable cover 55, the detachable cover 55 can be easily grasped with one hand. The handling ripples 59 further improve the grip. The detachable cover 55 and the actuation element 61 are made from plastic which is easy to manufacture and provides a pleasant handling. In addition to the handling ripples 59 the outer surface can be made slightly rough or provided with a colour that provides a slightly roughened surface.

Figure 5:
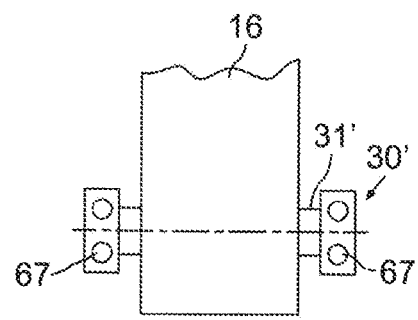
FIG. 5 shows a portion of an illumination bar of the UV reflection tester.

FIG. 5 shows a portion of a further embodiment of an illumination bar 16 for use in the embodiment of FIGS. 1 to 3. In this embodiment, the actuation disks 30' of the actuation bar 31' comprise ball bearings 67. In this way, the actuation disks 30' can move more easily on the ramp 50 of the detachable cover 55, which is not shown in FIG. 5.

FIGS. 6 to 9 show a second embodiment of a UV reflection tester 10', which comprises a pivotable cover 55'. The pivotable cover 55' comprises a battery compartment, which is not shown in FIG. 6, an indicator area 21 and a UV tube lamp 34. A switch 68 is provided at a ceiling surface 69 of the pivotable cover 55'. The switch 68 comprises a lever and a press button, which is arranged underneath the lever. When the pivotable cover 55' is closed, the lever is pressed to close the switch 68.

Preferentially, the covers 55, 55' in the embodiments of the present specification are opaque to light, for example they can be made of a black colour plastic material. The covers may also comprise parts which are transparent to visible or infrared light but opaque to ultraviolet light.

The bottom portion 12 of the UV reflection tester 10' is similar to the base portion 12 of the reflection tester 10. Different from the reflection tester 10, the specimen holder 18 is moved up and down with two thumb sliders 70 which are provided at each side of the casing.

FIG. 7 shows an isometric view of the pivotable cover 55' of FIG. 6. The UV tube lamp 34 is screwed into a bottom surface 72 of a compartment 73. A hinge protrusion 71 is provided at the ceiling surface 69 which can also be seen in FIG. 7, and which engage with a corresponding hinge portion of the plastic casing 11'.

FIG. 8 shows a cross sectional view of the UV reflection tester 10' of FIG. 6. The features of FIG. 8 can also be combined with the embodiment of FIG. 1.

In the embodiment of FIG. 8, a plate 74 of the specimen holder 18 has an attachment portion 8 that surrounds a vertical pole 75. Square bars 85 are provided at opposite sides of the attachment portion 8 and engage with corresponding openings in the thumb sliders 70. The thumb slider 70 is shown in FIG. 9. A second biasing spring 52 in the form of a coil spring is arranged around the vertical pole 75.

A main circuit board 76, which is arranged vertically in the plastic casing 11', is connected to a connection socket 77, to a capacitor 78, to the circuit board 44 of the sensor unit 17, and to the tube lamp 34. A transformer 79 is provided on the main circuit board 76 and electrically connected to the connected socket, to indicator lights of an indicator area 21, to an on/off switch 20 and to other electronic components of the main circuit board 76, which are not shown in FIG. 8.

The indicator area 21 and the on/off switch 20 are connected to the main circuit board 76 by a serial cable or flat cable, which is indicated in FIG. 8 by diagonal lines. The indicator lamps, which can be provided by indicator LEDs, indicate whether the specimen is an earth mined diamond or whether the specimen is HPHT/CVD diamond or a Type IIa/IaB diamond.

Similar to the plastic casing 11, the plastic casing 11' comprises two half portions which are connected to each other along a vertical separation area. The two half portions are screwed to each other at the screw holes 81, 82, 83. Furthermore, a horizontal plate 80 is provided, which engages into each of the half portions. The horizontal plate 80 can align the half portions to each other and provide stabilization.

FIG. 9 shows a further view of the UV reflection tester 10' of FIG. 6. In the example of FIG. 9, a ring 84 with a gemstone is arranged on the holder ring 40, which is moved into a testing position.

The operation of the UV tester 10' according to the second embodiment is now explained with reference to FIGS. 6 to 9.

First, the pivotable cover 55' is opened. Then, the specimen holder 18 is moved down using the thumb sliders 70. The specimen is placed into one of the pockets 41 of the specimen holder 18. The pivotable cover 55' is closed, the UV lamp 34 is activated, the signal from the sensor unit 17 is evaluated and the result is displayed in the indicator area 21.

FIGS. 10 to 18 show a third embodiment of a UV reflection tester 10″, which is similar to the embodiment of FIGS. 6 to 9. The design of the sensor unit 17′, which is shown in more detail in the FIGS. 10 to 13, is different from the embodiment of FIGS. 6 to 9. Among others, an LED ring 86 is provided around the detector tube 23 at a lower surface of the sensor unit 17′. The LED ring 86 provides visible and infrared light.

In one embodiment, the LED ring 86 comprises an alternating arrangement of visible light LEDs 97 and infrared LEDs 98. In another embodiment, which is not shown in the figures, the LED ring 86 comprises only visible light LEDs 97 or only infrared light LEDs 98.

FIG. 11 shows a sectional view of the UV reflection tester 10″ of FIG. 10. For illustration purposes, a support structure 87 of the tube lamp 34 is shown in cross sectional view. The tube lamp 34 and the support structure 87 are slightly inclined with respect to a vertical direction. Thereby, more UV light can be reflected upwards from the specimen through the detector tube 23 onto a UV light detector on top of the detector tube 23.

FIG. 12 shows a further sectional view of the UV reflection tester 10″ of FIG. 10, in which a gemstone on a ring 84 is clamped between the holder ring 40 and the detector tube 23 in a testing position.

FIG. 13 shows an enlarged sectional view of FIG. 10 of the UV reflection tester 10″ of FIG. 10, in which the sensor unit 17′ is drawn transparent in order to illustrate a revolver mechanism for moving light sensors into a predetermined position. As shown in FIG. 13, three light detectors 89 are provided on a revolver disk 88, a visible light detector, an infrared light detector and an ultraviolet light detector. The revolver disk 88 is supported such that it is rotatable around its axis and is connected to an electric stepper motor, which is shown in FIG. 18.

The operation of the UV reflection tester 10″ according to the third embodiment is now explained with reference to FIGS. 10 to 13. Depending on a selected operation mode, the stepper motor rotates the revolver disk 88 around its axis such that one of the light detectors 89 is positioned above the detector tube 23. In an IR testing mode or in a visible light testing mode the operation of the UV reflection tester 10″ is as follows.

The revolver disk 88 is rotated until the visible light detector or the infrared light detector is positioned above the detector tube 23. The specimen holder 18 and thereby the specimen is moved downwards a predetermined distance away from detector tube 23. In a next step, the LED ring 86 is illuminated. Light from the LED ring 86 passes through the specimen and is directed through the detector tube 23 onto the corresponding detector.

In an UV testing mode, the operation of the UV reflection tester 10″ of FIGS. 10 to 13 is as follows.

The revolver disk 88 is rotated until the UV light detector is positioned above the detector tube 23. The specimen holder 18 is moved into a clamping position, in which the specimen touches the detector tube 23. In a next step, the tube lamp 34 is illuminated. Light from the tube lamp 34 passes through the specimen and is directed through the detector tube 23 onto the UV light detector.

Referring to the above-mentioned UV reflection testers 10, 10′, 10″ of an embodiment of this specification, its operation, during a reflection test of a specimen, follows an automated sequence which is carried out according to a computer program on an electronic component of the UV reflection tester 10, 10′, 10″. A user action, such as closing the detachable cover 55 and pressing a button, triggers the automated sequence.

FIG. 14 shows a revolver mechanism 90 for use in the reflection tester 10″ of FIGS. 10 to 13. A revolver table 94 holds a UV light detector 91, an IR light detector 92 and a visible light detector 93. The detectors are aligned at about 120 degrees from each other around a rotation centre. A shaft, which is not shown in FIG. 14, is attached to the revolver table 94 at the rotation centre. The detectors 91, 92, 93 each comprise two connection pins 95 at their respective upper ends. In one embodiment, the connection pins 95 are connected to cables which are soldered to the connection pins 95.

FIG. 15 shows an LED ring 86. The LED ring 86 comprises a ring-shaped holder 99 on which visible light LEDs 97 and IR LEDs 98 are arranged for use in the reflection tester 10″ of FIGS. 10 to 13. The LEDs 97, 98 are connected to a power supply cable 100.

FIG. 16 shows a top view of a revolver mechanism 90 of FIG. 14. As shown in FIG. 16 the connection pins 95 are connected to cables 101.

FIG. 17 shows a side view of the revolver mechanism 90 of FIG. 14 and a portion of the reflection tester 10″.

The revolver table 94 is connected to a shaft, a gear and a stepper motor. These elements are not shown in FIGS. 16 and 17 but they are shown in FIG. 18, by way of example.

FIG. 18 shows a further embodiment of a revolver mechanism 90′ and a portion of the reflection tester 10″. In the embodiment of FIG. 18 the detectors 91, 92, 93 are not permanently connected to cables 101, as in the previous embodiment, but by way of two contact portions 102 which provide an electric contact to a detector 91, 92, 93 in a detection position when the detector 91, 92, 93 is positioned above the detection tube 23.

A rotation shaft 103 is connected to the revolver table 94. The rotation shaft 103 is mechanically connected to an output of a stepper motor 104 over tooth wheels 105, 106. The stepper motor 104 is connected to a control circuit of the reflection tester 10″ over power supply cables, which are not shown in FIG. 18.

FIG. 19 shows an improved diamond tester 210. The diamond tester 210 is also called a diamond testing device. The diamond tester 210 is also called a UV reflection tester.

As seen in FIG. 21, the diamond tester 210 includes a movable specimen holder 213, a stationary illumination unit 216, a stationary ultraviolet (UV) light sensor unit 220, and a casing 227. As seen in FIG. 23, the diamond tester 210 also includes an electronic evaluation module 224.

The electronic evaluation module 224 is electrically connected to the stationary illumination unit 216 and to the stationary light sensor unit 220. The electronic evaluation module 224 is placed inside the casing 227. The specimen holder 213, the illumination unit 216, and the light sensor unit 220 are attached to an outer surface of the casing 227.

As seen in FIG. 19, referring to the casing 227, it includes a base unit 227-1 with a rotatable or pivotable cover unit 227-2.

The base unit 227-1 has a horizontal base part 227-1A and a vertical base part 227-1B. The vertical base part 227-1B is also called a side portion. Each of the horizontal base part 227-1A and the vertical base part 227-1B has a general rectangular shape. One end of the horizontal base part 227-1A is attached to a lower end of vertical base part 227-1B such that the base unit 227-1 has a L shape.

The rotatable cover unit 227-2 has an upper cover part 227-2A and a lower cover part 227-2B.

Each of the upper cover part 227-2A and the lower cover part 227-2B has a general rectangular shape. An upper end of the lower cover part 227-2B is attached to a first end of the upper cover part 227-2A such that the rotatable cover unit 227-2 has an L shape.

With respect to the base unit 227-1, a second end of the upper cover part 227-2A of the cover unit 227-2 is rotatably attacked to an upper end of the vertical base part 227-1B of the base unit 227-1.

The base unit 227-1 is rotatably attached to the cover unit 227-2 to provide a closed and an open position. The closed position is shown in FIG. 23 while the open position is shown in FIGS. 19, 20, 21, and 22.

In the closed position, the cover unit 227-2 and the base unit 227-1 enclose or surround a specimen testing area 230. The specimen holder 213, the illumination unit 216, and the stationary light sensor unit 220 are placed in the specimen testing area 230.

Referring to the specimen holder 213, it includes a vertically movable specimen receiving unit 213-1, a spring unit 213-2, and a movable specimen positioning button 213-3. The specimen receiving unit 213-1, the spring unit 213-2, and the movable specimen positioning button 213-3 are shown in FIG. 23. The spring unit 213-2 is attached to the specimen receiving unit 213-1 and to the movable specimen positioning button 213-3.

The specimen receiving unit 213-1 is provided in the specimen testing area 230 and it is placed next to the vertical base part 227-1B. The specimen receiving unit 213-1 includes a rotatable holder ring 213-1A and a stationary inner cylinder 213-1B, which is inserted into the holder ring 213-1A. The stationary inner cylinder 213-1B and the holder ring 213-1A have the same horizontal axis. The rotatable holder ring 213-1A rotatably engages with the stationary inner cylinder 213-1B.

In particular, the holder ring 213-1A comprises a cylinder with six different pockets P, which are placed in an outer surface of the cylinder. The pockets P are also called specimen receiving areas. The pockets P are illustrated in FIGS. 19 and 21.

The pockets P are suitable for receiving a loose diamond specimen and for receiving a mounted diamond specimen. The diamond specimen can be mounted on a ring, a necklace, a pendant, a bracket, or an earring.

Three pockets P are formed as three conical shapes of varied sizes that are suitable for receiving a diamond specimen with a cone base portion.

One pocket P is provided as a rectangular wedge that is suitable for receiving a diamond specimen with an elongated wedge shape base.

Two remaining pockets P are provided as an elongated recess with an elongated opening that are suitable for receiving an elongated straight stud of an earring.

The spring unit 213-2 is placed inside the vertical base part 227-1B and it acts to push or bias the holder ring 213-1A of the specimen receiving unit 213-1 vertically upwards to a predetermined specimen testing position.

The specimen positioning button 213-3 is placed next to an outer surface of the vertical base part 227-1B.

Referring to the illumination unit 216, it includes a stationary ultraviolet (UV) light emitting diode (LED) light source 216-1, as seen in FIG. 23. The light source is also called a lamp.

The stationary UV LED light source 216-1 is provided in the specimen testing area 230 and it is placed next to the vertical base part 227-1B. The UV LED light source 216-1 is attached to an outer surface of the vertical base part 227-1B of the base unit 227-1. The UV LED light source 216-1 is positioned slightly away from a vertical axis that passes the predetermined specimen testing position. Put differently, the LED light UV source 216-1 is positioned beside the vertical axis and the UV LED light source 216-1 is positioned near the predetermined specimen testing position. Moreover, the UV LED light source 216-1 is positioned such that light rays, which are produced by the UV LED light source 216-1, are directed at the predetermined specimen testing position, as shown in FIG. 24.

Referring to the stationary light sensor unit 220, it includes an elongated detector tube 220-1, a stationary UV light detector 220-2, and a sensor housing 220-3. The detector tube 220-1 is also called a detection tip or a light guide.

The sensor housing 220-3 is attached to an outer surface of the vertical base part 227-1B of the base unit 227-1.

The detector tube 220-1 is positioned vertically. An upper end of the detector tube 220-1 is attached to a bottom part of the sensor housing 220-3 such that a lower end of the detector tube 220-1 is placed directly above the above-mentioned predetermined specimen testing position.

The detector tube 220-1 is also placed near the stationary UV LED light source 216-1. The detector tube 220-1 is separated from the stationary UV LED light source 216-1 by a predetermined separation distance. In this embodiment, the predetermined separation distance is about one centimetre.

The UV light detector 220-2 is placed inside the sensor housing 220-3 and is placed vertically above the detector tube 220-1 and is also placed vertically above the predetermined specimen testing position.

Referring to the electronic evaluation module 224, it includes a computing processor 224-1, a pair of indicator light sources 224-2A and 224-2B, a test activation button 224-3, and a cover position switch 224-4. The electronic evaluation module 224 is shown in FIG. 23.

The computing processor 224-1 is placed inside the casing 227. In a general sense, the processor 224-1 can be placed either inside the base unit 227-1 or inside the cover unit 227-2 of the casing 227.

The indicator light sources 224-2A and 224-2B are placed below a transparent or translucent indicator area of a top surface of the cover unit 227-2.

The test activation button 224-3 is placed on the top surface of the cover unit 227-2.

The cover position switch 224-4 is placed on an inner surface of the cover unit 227-2.

The processor 224-1 is electrically connected to the indicator light sources 224-2A and 224-B and to the test activation button 224-3. The processor 224-1 is also electrically connected to the stationary UV LED light source 216-1 of the illumination unit 216 and to the stationary UV light detector 220-2 of the light sensor unit 220.

In use, the diamond tester 210 is used for evaluating a diamond specimen.

The diamond tester 210 provides a specimen receiving mode and a specimen evaluation mode.

In the specimen receiving mode, a user places the base unit 227-1 of the casing 227 on a flat horizontal surface. In a general sense, the base unit 227-1 can also be placed in an inclined surface.

The cover unit 227-2 is then rotated to an open position, wherein the upper cover part 227-2A of the cover unit 227-2 is rotated away from the horizontal base part 227-1A of the base unit 227-1.

In this open position, the base unit 227-1 does not push or compress the cover position switch 224-4, thereby placing the cover position switch 224-4 in an open state.

In a general sense, the cover position switch 224-4 can also be constructed that it is placed in a closed state, instead of the open state, when it is not pushed by an object or user.

The user then moves or actuates the specimen positioning button 213-3 vertically downwards, wherein the button 213-3 moves the spring unit 213-2, which, in turn, moves the specimen receiving unit 213-1 downward.

After this, the user rotates the holder ring 213-1A of the specimen receiving unit 213-1 about the inner cylinder 213-1B such that a desired pocket of the holder ring 213-1A is placed at a predetermined rotary testing location. At this location, the desired pocket is placed above the other pockets P.

As seen in FIG. 24, the user then places a diamond specimen S in the desired pocket, which is positioned at the predetermined rotary testing location. A table of the diamond specimen S, which refers to a largest facet of the diamond specimen S, is then facing upwards. The table acts as a top surface of the diamond specimen S.

The user later ceases actuating the specimen positioning button 213-3, wherein the spring unit 213-2 afterward pushes and moves the specimen receiving unit 213-1 to the predetermined specimen testing position. In this position, the lower end of the detector tube 220-1 touches and contacts the top surface of the diamond specimen S.

In the specimen evaluation mode, the cover unit 227-2 is rotated to a closed position, wherein the upper cover part 227-2A of the cover unit 227-2 is rotated towards the horizontal base part 227-1A of the base unit 227-1. The upper cover part 227-2A is also positioned across from the horizontal base part 227-1A and it also positioned above the horizontal base part 227-1A.

In this closed position, the cover unit 227-2 covers and encloses the specimen receiving unit 213-1 and the diamond specimen S such that external or surrounding light rays are blocked and prevented from reaching the diamond specimen S. In other words, the diamond specimen S is covered in darkness.

Moreover, in this position, the base unit 227-1 also presses the cover position switch 224-4, such that the cover position switch 224-4 changes from an open state to a closed state. The closed state of the cover position switch 224-4 indicates that the cover unit 227-2 is closed.

A user then issues a specimen evaluation instruction by pressing the test activation button 224-3.

The processor 224-1 later detects that the test activation button 224-3 is being pressed and the cover position switch 224-4 is in the closed state.

The processor 224-1 then activates the stationary UV LED light source 216-1, which subsequently generates UV light rays that are shone at the diamond specimen S. In other words, the generated UV light rays travel to the diamond specimen S.

The generated UV light rays have a wavelength range from 240 nm to 268 nm, especially in a range about 254 nm. For example, the wavelength can have a range of 254+/−10 nm or a range of 254+/−5 nm. In this example, the range is defined as a light frequency range which contains 90% of luminous flux or a light frequency range in which light intensity is more than 5% of the peak light intensity.

The UV light rays then travel to the diamond specimen S. Some UV light rays are then reflected from the diamond specimen S. The reflected UV light rays can enter the lower end of the detector tube 220-1, travel through the detector tube 220-1 to reach the stationary UV light detector 220-2.

If the diamond specimen S is a type IIa, IaB, HPHT (High Pressure High Temperature), or CVD (Chemical Vapor Deposition) diamond, the diamond specimen S would reflect most or more of the UV light rays into the detector tube 220-1.

Different from a natural or geological process, the HPHT diamond refers to an artificial diamond that is produced using a high pressure and high temperature process. The CVD diamond refers to an artificial diamond that is produced using a chemical vapor deposition crystal formation process.

If the diamond specimen S is type IaA, IaAB, or Ib diamond, it would reflect little or no UV light rays into the detector tube 220-1.

The stationary UV light detector 220-2 then measures intensity of the reflected UV light rays and sends the light intensity measurements to the processor 224-1.

The processor 224-1 then evaluates the measurements and activates the indicator light sources 224-2A and 224-2B according to results of the evaluations, for viewing by the user.

When the evaluation shows that specimen is a type IIa, IaB, HPHT, or CVD diamond, the processor 224-1 then activates the indicator light source 224-2A.

When the evaluation shows that specimen is a type IaA, IaAB, or Ib diamond, the processor 224-1 activates the indicator light source 224-2B.

The diamond tester 210 provides several benefits.

The UV LED light source 216-1 generates UV light rays in a brief time. This is different from light sources that uses other technology that has a long warm up time. This, in turn, allows for a quick evaluation of the diamond specimen.

The UV LED light source 216-1 is placed near the diamond specimen and near the detector tube 220-1 for more efficient illumination of the diamond specimen.

The UV LED light source 216-1 and the detector tube 220-1 are also stationary, thereby improving reliability of the diamond tester 210. This is different from other tester, wherein its light source is attached a moving part of the tester. In use, the movement of the part can cause the tester to fail earlier.

This diamond tester 210 provides diamond evaluation result quickly. The user can be trained quickly to use the diamond tester 210. A long training is thus not needed to differentiate between different types of diamond, which includes synthetic diamonds.

FIGS. 25 and 27 show an improved diamond tester 210'. The diamond tester 210' is a variation of the diamond tester 210 of FIG. 19. The diamond testers 210' and 210 have similar parts.

The diamond tester 210' includes a movable specimen holder 213', a stationary illumination unit 216', a stationary ultraviolet (UV) light sensor unit 220', a casing 227', and an electronic evaluation module. The electronic evaluation module is not show in FIGS. 25 and 27.

The electronic evaluation module is electrically connected to the stationary illumination unit 216' and to the stationary light sensor unit 220'. The electronic evaluation module is placed inside the casing 227'. The specimen holder 213', the illumination unit 216', and the light sensor unit 220' are attached to an outer surface of the casing 227'.

Referring to the casing 227', it includes a stationary base unit 227-1' with a rotatable cover unit 227-2'.

The base unit 227-1' has a horizontal base part 227-1A' and a vertical base part 227-1B'.

The horizontal base part 227-1A' has a general shape of a disc. The vertical base part 227-1B' has a general shape of one half of a cylinder, the cylinder being divided longitudinally. A top surface of the horizontal base part 227-1A' is attached to a lower end of the vertical base part 227-1B'.

The rotatable cover unit 227-2' includes a partial hollow cylinder with a flat top sheet and a vertical curve sheet. A top part of the vertical curve sheet is attached to an edge of the flat top sheet. The cover unit 227-2' is rotatably connected to the base unit 227-1' via a vertical pin 227-3' such that the cover unit 227-2' can rotate about a vertical axis of the horizontal base part 227-1A'.

The arrangement of the cover unit 227-2' with the base unit 227-1' provides a closed and an open position. The open position is shown in FIGS. 25 and 27.

In the closed position, the cover unit 227-2' and the base unit 227-1' enclose or surround a specimen testing area 230'. The specimen holder 213', the illumination unit 216', and the stationary light sensor unit 220' are placed in the specimen testing area 230'. The specimen testing area 230' is shown in FIGS. 25 and 27.

Referring to the specimen holder 213', it includes a vertically movable specimen receiving unit 213-1', a spring unit, and a movable specimen positioning button. The specimen receiving unit 213-1' is shown in FIG. 26 while the spring unit, and the movable specimen positioning button are not shown in the FIG. 26.

As seen in FIGS. 25 and 27, the specimen receiving unit 213-1' is provided in the specimen testing area 230' and it is placed next to the vertical base part 227-1B'.

As seen in FIG. 26, the specimen receiving unit 213-1' includes a rotatable holder ring 213-1A' and a stationary inner cylinder 213-1B'. The holder ring 213-1A' comprises a cylinder with different pockets P'.

The spring unit is placed inside the vertical base part 227-1B'. The specimen positioning button is placed next to an outer surface of the vertical base part 227-1B'.

Referring to the illumination unit 216', it includes a stationary ultraviolet (UV) light emitting diode (LED) light source 216-1', as seen in FIG. 26. As seen FIGS. 25 and 27, the stationary UV LED light source 216-1' is provided in the specimen testing area 230' and it is placed next to the vertical base part 227-1B'.

Referring to the stationary light sensor unit 220', it includes an elongated detector tube 220-1', a stationary UV light detector, and a sensor housing 220-3', as seen in FIG. 26. The stationary UV light detector is not shown in FIG. 26.

Referring to the electronic evaluation module, it includes a computing processor, a pair of indicator light sources, a test activation button, and a cover position switch.

The casing 227' can provide a large specimen testing area 230', thereby allowing large jewelry, such as necklace, pendant, or bracket, to be tested.

The subject matter of the present specification is also disclosed in the following list organized into items. The items refer to features or elements. The respective combinations of features, which are disclosed in the item list, are regarded as independent subject matter, respectively, that can also be combined with other features of the application.

Item List 1

1. A diamond testing device comprising
    a casing, which comprises
        a base unit with a cover unit being pivotably attached to the base unit, the casing provides a closed position, wherein the casing encloses a specimen testing area,
    a movable specimen holder, which comprises
        a specimen receiving unit being movable attacked to the base unit and being provided in the specimen testing area for receiving a diamond specimen and
        a resilient element being provided inside the base unit for pushing the specimen receiving unit to a predetermined specimen testing position,
    an illumination unit, which comprises
        a ultraviolet (UV) light emitting diode (LED) light source being attached to the base unit and being provided above the predetermined specimen testing position for generating UV light rays with a predetermined light intensity, the UV light rays being directed at the predetermined specimen testing position,
    a light sensor unit, which comprises
        an elongated detector tube being attached to the base unit, provided near the UV LED light source, and above the predetermined specimen testing position for receiving the UV light rays being reflected from the diamond specimen, and
        a light detector for measuring intensity of the UV light rays from the detector tube, and
    a computing processor being provided for
        activating the LED light source,
        receiving measurements from the light detector, and
        sending out a result signal according to the measurements.

2. The diamond testing device according to item 1, wherein the movable specimen holder further comprising a movable specimen positioning button being provided next to an outer surface of the base unit for moving the resilient element and the movable specimen receiving unit away from the predetermined specimen testing position.

3. The diamond testing device according to item 1 or 2, wherein
    the resilient element comprises a spring unit.

4. The diamond testing device according to one of items 1 to 3, wherein
    the specimen receiving unit comprises a rotatable holder ring with at least one specimen receiving area for receiving a diamond specimen.

5. The diamond testing device according to item 4, wherein the specimen receiving area comprises a recess with an opening for receiving a stud of an earring.

6. The diamond testing device according to item 4 or 5, wherein
    the specimen receiving unit further comprises a stationary inner cylinder that is inserted inside the holder ring for engaging the holder ring.

7. The diamond testing device according to one of items 1 to 6, wherein
    the light sensor unit further comprises a sensor housing for enclosing the light detector.

8. The diamond testing device according to one of items 1 to 7, wherein
    the detector tube is positioned for contacting the diamond specimen, which is provided in the specimen receiving area of the specimen receiving unit that is provided in the predetermined specimen testing position.

9. The diamond testing device according to one of items 1 to 8 further comprising
    a plurality of indicator light sources being provided on the casing for being activated according to the result signal.

10. The diamond testing device according to one of items 1 to 9 further comprising
a test activation button being providing on the casing for allowing a user to send a test activation signal to the computing processor.

12. The diamond testing device according to one of items 1 to 11 further comprising
a cover position switch for providing an indication of a position of the casing to the computing processor.

13. The diamond testing device according to one of items 1 to 12, wherein
the base unit comprises a horizontal base part and a vertical base part, one end of the horizontal base part is attached to a lower end of vertical base part such that the base unit has a L shape,
the cover unit comprises a lower cover part and an upper cover part, an upper end of the lower cover part being attached to a first end of the upper cover part such that the cover unit has an L shape, and
a second end of the upper cover part being pivotable attacked to an upper end of the vertical base part.

14. The diamond testing device according to one of items 1 to 12, wherein
the cover unit being rotatably connected to the base unit via a vertical pin.

Item List 2

1. A diamond testing device comprising
a casing with an opening, the opening defining a testing area,
a specimen holder with a resilient means, the specimen holder being movable attached to the casing and being provided in the testing area for receiving a specimen,
a cover with an ultraviolet (UV) lamp, the UV lamp being provided for illuminating the specimen, the cover being pivotably attached to the casing for shielding a user from light rays of the UV lamp,
a light sensor unit being attached to the casing and being provided in the testing area, the light sensor unit comprises an UV light sensor, the specimen holder being biased towards the light sensor unit by the resilient means, and
an evaluation board for evaluating the specimen according to signals from the light sensor unit.

2. A diamond testing device comprising
a casing with an opening, the opening defining a testing area,
a specimen holder with a resilient means, the specimen holder being movable attached to the casing and being provided in the testing area for receiving a specimen,
an illumination bar with an ultraviolet (UV) lamp, the illumination bar being pivotably attached to the casing for illuminating the specimen,
a detachable cover being provided for shielding a user from light rays of the UV lamp,
a light sensor unit being attached to the casing and being provided in the testing area, the light sensor unit comprises an UV light sensor, the specimen holder being biased towards the light sensor unit by the resilient means, and
an evaluation board for evaluating the specimen according to signals from the light sensor unit.

3. The diamond testing device according to item 1 or 2, wherein
the light sensor unit comprises at least one long wavelength light sensor, and
the diamond testing device comprises a long wavelength illumination unit.

4. The diamond testing device according to item 3, wherein the long wavelength light sensor and the ultraviolet light sensor are provided on a revolver table with a revolver mechanism.

5. The diamond testing device according to item 3 or 4, wherein
the long wavelength light sensor comprises a visible light sensor and
the long wavelength illumination unit comprises a visible light emitter.

6. The diamond testing device according to item 5, wherein the visible light emitter is provided as a Light Emitting Diode (LED).

7. The diamond testing device according to one of the items 3 to 6, wherein
the long wavelength light sensor comprises an infrared light sensor and
the long wavelength illumination unit comprises an infrared light emitter.

8. The diamond testing device according to item 7, wherein the infrared light emitter is provided as an LED.

9. The diamond testing device according to one of the items 5 to 8, wherein
the long wavelength illumination unit comprises a ring-shaped holder with alternating visible light emitters and infrared light emitters.

10. The diamond testing device according to item 9, wherein the ring-shaped holder surrounds the light sensor unit.

11. The diamond testing device according to one of the items 3 to 10, wherein
wherein the at least one long wavelength light sensor and the UV light sensor are movable to a detection/testing position that is provided above the sensor tube.

12. The diamond testing device according to one of the items 1 to 11, comprising
an electronic circuit that is adapted to move the specimen holder into a long wavelength testing position, the long wavelength testing position being provided at a predetermined distance away from (a tip of) the light sensor unit.

13. The diamond testing device according to one of the items 1 to 12, wherein
the light sensor unit comprises a sensor tube.

14. The diamond testing device according to one of the items 1 to 13, wherein
the light sensor unit comprises a testing tube which protrudes towards the specimen holder.

15. The diamond testing device according to one of the items 1 to 14, wherein
the resilient means comprises a spring.

16. The diamond testing device according to one of the items 1 to 15, comprising
an accumulator for energizing the UV lamp, the accumulator being connected to an electrical high-power circuit.

17. The diamond testing device according to one of the items 1 to 16, wherein
the UV lamp is provided as a tube lamp.

18. The diamond testing device according to one of the items 1 to 16, wherein
the UV lamp is provided as an UV LED.

19. The diamond testing device according to one of the items 1 to 18, wherein
the UV lamp generates light rays with a wavelength, which ranges from about 240 nm to about 268 nm.
20. The diamond testing device according to one of the items 5 to 19, wherein
the visible light emitter generates light rays with a wavelength, which ranges from about 380 nm to about 780 nm.
21. The diamond testing device according to one of the items 7 to 20, wherein
the infrared light emitter generates light rays with a wavelength, which ranges from about 750 nm to about 1,000,000 nm.

Although the above description contains much specificity, this should not be construed as limiting the scope of the embodiments but merely providing illustration of the foreseeable embodiments. The above stated advantages of the embodiments should not be construed especially as limiting the scope of the embodiments but merely to explain possible achievements if the described embodiments are put into practice. Thus, the scope of the embodiments should be determined by the claims and their equivalents, rather than by the examples given.

REFERENCE NUMBERS 8 attachment portion
9 inner side
10, 10' UV reflection tester
11, 11' plastic casing
12 bottom portion
13 side portion
14 top portion
15 U-shaped recess, testing area
16 illumination bar
17, 17' sensor unit
18 specimen holder
19 top surface
20 on/off switch
21 indicator area
22 push button
23 sensor tip/detector tube
24 inner side casing
25 double arrow
26 double arrow
27 up/down movement
28 engagement ledge
29 engagement recess
30, 30' actuation disk
31, 31' actuation bar
32 base portion
33 head portion
34 tube lamp/UV lamp
35 power electronic circuit
36 intermediate component
37 upper portion
38 cone shaped portion
39 inner cylinder
40 holder ring
41 pocket
42 lower portion
43 UV detector
44 circuit board
45 upper part
46 gemstone
47 testing platform
48 front part
49 attachment portion
50 ramp
51 first biasing spring
52 second biasing spring
53 holding bar
54 vertical slit
55 detachable cover
55' pivotable cover
56 rim
57 rectangular protrusion
58 ridge
59 handling ripple
60 outer surface
61 actuation element
62 ramp shaped portion
63 inner side of ledge
64 elongated recess
65 outer side of ledge
66 engagement slot
67 ball bearing
68 switch
69 ceiling surface
70 thumb sliders
71 hinge protrusion
72 bottom surface
73 compartment
74 plate
75 vertical pole
76 main circuit board
77 connection socket
78 capacitor
79 transformer
80 horizontal plate
81 screw hole
82 screw hole
83 screw hole
84 ring
85 square bars
86 LED ring
87 support structure
88 revolver disk
89 light detector
90 revolver mechanism
91 UV light detector,
92 IR light detector,
93 visible light detector
94 revolver table
95 connection pins
97 visible light LED
98 IR LED
99 ring-shaped holder
100 power supply cable
101 cables
102 contact portion
103 rotation shaft
104 stepper motor
105, 106 tooth wheels
210 diamond tester
210' diamond tester
213 specimen holder
213' specimen holder
213-1 specimen receiving unit
213-1' specimen receiving unit
213-1A holder ring
213-1A' holder ring
213-1B inner cylinder 213-1B' inner cylinder
213-2 spring unit
213-3 specimen positioning button
216 illumination unit
216' illumination unit
216-1 UV LED light source
216-1' UV LED light source
220 light sensor unit
220' light sensor unit
220-1 detector tube
220-1' detector tube
220-2 UV light detector
220-3 sensor housing
220-3' sensor housing
224 electronic evaluation module
224-1 processor
224-2A indicator light source
224-2B indicator light source
224-3 test activation button
224-4 cover position switch
227 casing
227' casing
227-1 base unit
227-1' base unit
227-1A horizontal base part
227-1A' horizontal base part
227-1B vertical base part
227-1B' vertical base part
227-2 rotatable cover unit
227-2' rotatable cover unit
227-3' pin
227-2A upper cover part
227-2B lower cover part
230 specimen testing area
230' specimen testing area
P pocket
P' pocket
S diamond specimen

The invention claimed is:

1. A diamond testing device comprising:
a casing, which comprises
a base unit with a cover unit being pivotably attached to the base unit, the casing provides a closed position, wherein the casing encloses a specimen testing area;
a movable specimen holder, which comprises
a specimen receiving unit being moveable attached to the base unit and being provided in the specimen testing area for receiving a diamond specimen, and
a resilient element being provided inside the base unit for pushing the specimen receiving unit to a predetermined specimen testing position;
an illumination unit, which comprises
an ultraviolet (UV) light emitting diode (LED) light source being attached to the base unit and being provided above the predetermined specimen testing position for generating UV light rays with a predetermined light intensity, the UV light rays being directed at the predetermined specimen testing position;
a light sensor unit, which comprises
an elongated detector tube being attached to the base unit, provided near the UV LED light source, and above the predetermined specimen testing position for receiving the UV light rays being reflected from the diamond specimen, and
a light detector for measuring intensity of the UV light rays from the detector tube; and
a computing processor being provided for
activating the UV LED light source,
receiving measurements from the light detector, and
sending out a result signal according to the measurements;
wherein the specimen receiving unit comprises a rotatable holder ring with a plurality of specimen receiving areas for receiving the diamond specimen.

2. The diamond testing device according to claim 1, wherein the movable specimen holder further comprising a movable specimen positioning button being provided next to an outer surface of the base unit for moving the resilient element and the movable specimen receiving unit away from the predetermined specimen testing position.

3. The diamond testing device according to claim 1, wherein the resilient element comprises a spring unit.

4. The diamond testing device according to claim 1, wherein the diamond specimen refers to a loose diamond specimen or to a mounted diamond specimen.

5. The diamond testing device according to claim 4, wherein the specimen receiving area comprises a recess with an opening for receiving a stud of an earring.

6. The diamond testing device according to claim 4, wherein the specimen receiving unit further comprises a stationary inner cylinder that is inserted inside the holder ring for engaging the holder ring.

7. The diamond testing device according to claim 1, wherein the light sensor unit further comprises a sensor housing for enclosing the light detector.

8. The diamond testing device according to claim 1, wherein the detector tube is positioned for contacting the diamond specimen, which is provided in the specimen receiving area of the specimen receiving unit that is provided in the predetermined specimen testing position.

9. The diamond testing device according to claim 1, further comprising a plurality of indicator light sources being provided on the casing for being activated according to the result signal.

10. The diamond testing device according to claim 1, further comprising a test activation button being provided on the casing for allowing a user to send a test activation signal to the computing processor.

11. The diamond testing device according to claim 1, further comprising a cover position switch for providing an indication of a position of the casing to the computing processor.

12. The diamond testing device according to claim 1, wherein:
the base unit comprises a horizontal base part and a vertical base part, one end of the horizontal base part is attached to a lower end of vertical base part such that the base unit has a L shape; and
the cover unit comprises a lower cover part and an upper cover part, an upper end of the lower cover part being attached to a first end of the upper cover part such that the cover unit has an L shape, and a second end of the upper cover part being pivotably attached to an upper end of the vertical base part.

13. The diamond testing device according to claim 1, wherein the cover unit is rotatably connected to the base unit via a vertical pin.

14. A diamond testing device comprising:
a casing with an opening, the opening defining a testing area;

a specimen holder with a resilient means, the specimen holder being moveable attached to the casing and being provided in the testing area for receiving a specimen;

a cover with an ultraviolet (UV) lamp, the UV lamp being provided for illuminating the specimen, the cover being pivotably attached to the casing for shielding a user from light rays of the UV lamp;

a light sensor unit being attached to the casing and being provided in the testing area, the light sensor unit comprises an UV light sensor, the specimen holder being biased towards the light sensor unit by the resilient means; and an evaluation board for evaluating the specimen according to signals from the light sensor unit.

15. The diamond testing device according to claim 14, wherein the light sensor unit further comprises at least one long wavelength light sensor, and the diamond testing device further comprises a long wavelength illumination unit.

16. The diamond testing device according to claim 15, wherein the long wavelength light sensor and the ultraviolet light sensor are provided on a revolver table with a revolver mechanism.

17. The diamond testing device according to claim 15, wherein the long wavelength light sensor comprises a visible light sensor and the long wavelength illumination unit comprises a visible light emitter.

18. The diamond testing device according to claim 17, wherein the visible light emitter is provided as a Light Emit-ting Diode (LED).

19. The diamond testing device according to claim 17, wherein the visible light emitter generates light rays with a wavelength, which ranges from about 380 nm to about 780 nm.

20. The diamond testing device according to claim 15, wherein the at least one long wavelength light sensor and the UV light sensor are movable to a detection/testing position that is provided above the sensor tube.

21. The diamond testing device according to claim 14, wherein a ring-shaped holder surrounds the light sensor unit.

22. The diamond testing device according to claim 14, comprising an electronic circuit that is adapted to move the specimen holder into a long wavelength testing position, the long wavelength testing position being provided at a predetermined distance away from the light sensor unit.

23. The diamond testing device according to claim 14, wherein the light sensor unit comprises a sensor tube.

24. The diamond testing device according to claim 14, wherein the light sensor unit comprises a testing tube which protrudes towards the specimen holder.

25. The diamond testing device according to claim 14, wherein the resilient means comprises a spring.

26. The diamond testing device according to claim 14, comprising an accumulator for energizing the UV lamp, the accumulator being connected to an electrical high-power circuit.

27. The diamond testing device according to claim 14, wherein the UV lamp is provided as a tube lamp.

28. The diamond testing device according to claim 14, wherein the UV lamp is provided as an UV LED.

29. The diamond testing device according to claim 14, wherein the UV lamp generates light rays with a wavelength, which ranges from about 240 nm to about 268 nm.

* * * * *